United States Patent [19]

Medenica

[11] Patent Number: 5,482,711
[45] Date of Patent: Jan. 9, 1996

[54] **USE OF *NIGELLA SATIVA* TO INCREASE IMMUNE FUNCTION**

[76] Inventor: Rajko D. Medenica, One Ocean Point, Port Royal Plantation, Hilton Head Island, S.C. 29928

[21] Appl. No.: 111,631

[22] Filed: Aug. 25, 1993

[51] Int. Cl.$^6$ .................................................. A61K 35/78
[52] U.S. Cl. ....................................... 424/195.1; 514/885
[58] Field of Search .......................... 424/195.1; 514/885

[56] References Cited

U.S. PATENT DOCUMENTS

| | | | |
|---|---|---|---|
| 4,687,761 | 8/1987 | Liu | 514/26 |
| 4,945,115 | 7/1990 | Liu | 514/731 |

OTHER PUBLICATIONS

Elkadi et al. *71st Annual Meeting of the Federation of American Societies for Experimental Biology Washington D.C. Mar. 29–Apr. 2, 1987*, 46(4), 1222.
Elkadi et al. *Arch AIDS Res 1* (2–3), pp. 232–233, 1987.
Dey, K. L., and Bahadur, R., 1984, *Indigenous Drugs of India*, International Book Distributors, Dehradun, India.
Kirtikar, K. R., and Basu, B. D., 1987, *Indian Medicinal Plants*, vol. I, International Book Distributors, Dehradun, India.
Nadkarni, K. M., 1976, "*Crocus sativus, Nigella sativa,*" *Indian Materia Medica*, vol. I, K. M. Nadkarni (ed), Bombay Popular Prakashan, Bombay, India.
Agarwal, R.; Kharya, M.D. and Shrivastava, R., 1979, "Antimicrobial Anthelmintic Activites of the Essential Oil of *Nigella Sativa Linn.,*" *Indian J. Exp. Biol.* 17:1264–5.
Akhtar, M. S. and Riffat, S., 1991, "Field Trial of Saussurea Lappa Roots Against Nematoides and *Nigella Sativa* Seeds Against Cestodes in Children," J.P.M.A. 41(8):185–7.
al–Awadi, F. M.; Khatter, M. A. and Gumaa, K. A., 1985, "On the Mechanism of the Hypoglycaemic Effect of a Plant Extract," *Diabetologia* 28:432–4.
al–Awadi, F.; Fatania, H. and Shamte, U., 1991, "The Effect of a Plant's Mixture Extract on Liver Gluconeogenesis in Streptozotocin Induced Diabetic Rats," *Diabetes Res. (Scotland)* 18(4):163–8.
Aruna, K. and Sivaramakrishnan, V. M., 1990, "Plant Products as Protective Agents Against Cancer," *Indian J. Exp. Biol.* 28(11):1008–11.
Aruna, K. and Sivaramakrishnan, V. M., 1992, "Anticarcinogenic Effects of Some Indian Plant Products," *Fd. Chem. Toxic. (England)* 30(11) :953–6.
Bitterman, W. A.; Farhadian, H.; Abu Samra, C.; Lerner, D.; Amoun, H.; Krapf, D. and Makov, U. E., 1991, "Environmental and Nutritional Factors Significantly Associated with Cancer of the Urinary Tract among Different Ethnic Groups," *Urol. Clin. North Am.* 18(3):501–8.
Datta, A. K.; Biswas, A. K. and Ghosh, P. D., 1983, "Chromosomal Variations in Callus Tissues of Two Species of *Nigella,*" *The Nucleus* 26(3):173–7.
Elkadi, A. and Kandil, O., 1987, "The Black Seed *Nigella Sativa* and Immunity: Its Effects on Human Cell Subsets," *Fed.Proc.* 45(4):1222.
Finter, N. B., 1969, "Dye Uptake Methods for Assessing Viral Cytopathogenicity and Their Application to Interferon Assays," *J. Gen. Virol.* 5:419–427.2

Kumar, B. H. and Thakur, S. S., 1989, "Effect of Certain Non–Edible Seed Oils on Growth Regulation in Dysdercus Similis (F)," *J. Anim. Morphol. Physiol.* 36(2) pp. 209–218.
Medenica, R.; Alonso, K.; Huschart, T. and Tyler, K., 1990, "Tumor Tissue Culture for Determining Efficient Drug for Intra–Arterial, Intra–Hepatic Chemotherapy of Colon Carcinoma Liver Metastasis," *Abstract presented at Conference on Combining BRM with Cytotoxic in the Treatment of Cancer.*
Merkel, D. E., Dressler, L. G. and McGuire, W. L., 1987, "Flow Cytometry Cellular DNA Contents and Prognosis in Human Malignancy," *J. Clin. Oncol.*, 5:1690–1703.
Metcalf, D., 1984, *Clonal Culture of Hematopoietic Cells*, Elsevier/North American Biomedical Press.
Metcalf, D., 1985, "The Granulocyte–Macrophage Colony–Stimulating Factors," *Science* 229:16–22.
Nair, S. C.; Salomi, M. J.; Panikkar, B. and Pannikar, K. R., 1991, "Modulatory Effects of *Crocus Sativus* and *Nigella Sativa* Extracts on Cisplatin–Induced Toxicity in Mice," *J. Ethnopharmocol* 31(1): 75–83.
Salmon, S. E.; Hamburger, A. W.; Soehnlein, B.; Durie, B. G.; Alberts, D. S. and Moon, T. E., 1978, "Quantitation of Differential Sensitivity of Human–Tumor Stem Cells to Anticancer Drugs," *N. Eng. J. Med.* 298:1321–7.
Salomi, N. J.; Nair, S. C.; Jayawardhanan, K. K.; Varghese, C. D. and Panikkar, K. R., 1992, "Anititumour Principles from *Nigella Sativa* Seeds," *Cancer Lett.* 63(1):41–6.
Salomi, M. J.; Nair, S. C. and Panikkar, K. R., 1991, "Inhibitory Effects of *Nigella Sativa* and Saffron (*Crocus Sativus*) on Chemical Carcinogenesis in Mice," *Nutr. Cancer* 16(1): 67–72.
Sayed, M. D., "Traditional Medicine in Health Care," 1980, *J. Ethnopharmocol.* 2(1): 19–22.
Shayeb, N. A. and Mabrouk, S. S., 1984, "Utilization of Some Edible and Medicinal Plants to Inhibit Aflatoxin Formation," *Nutrition Reports International* 29(2): 273–289.
Siddiqui, M. B.; Alam, M. M.; Husain, W. and Sharma, G. K., 1988, "Ethno–medical Study of Plants Used for Terminating Pregnancy," *Fitoterapia* LIX(3): 250–2.
Srivastava, K. C., 1989, "Extracts from Two Frequently Consumed Spices–Cumin (*Cuminum cyminum*) and Turmeric (*Curcuma Longa*)–Inhibit Platelet Aggregation and Alter Eicosanoid Biosynthesis in Human Blood Platelets," *Prostaglandins Leukot Essent Fatty Acids* 37(1): 57–64.
Tennekoon, K. H.; Jeevathayaparan, S.; Kurukulasooriya, A. P. and Karunanayake, E. H., 1991, "Possible Hepatotoxicity of *Nigella sativa* Seeds and *Dregea Volubilis* Leaves," *J. Ethnopharmocol.* 31(3): 283–9.
Vihan, V. S. and Panwar, H. S., 1987, "Galactopoietic Effect of *Nigella Sativa* (*H–Kalonji*) in Clinical Cases of Agalactia in Goats." *Indian Vet. J.* 64:347–9.
Von Hoff, D. D.; Cowan, J.; Harris, G. and Reisdorf, G., 1981, "Human Tumor Cloning: Feasibility and Clinical Correlations," *Cancer Chemother. Pharmacol.* 6:265–271.

*Primary Examiner*—Douglas W. Robinson
*Assistant Examiner*—Howard C. Lee
*Attorney, Agent, or Firm*—DeWitt Ross & Stevens

[57] ABSTRACT

A pharmaceutical composition containing an extract of the plant *Nigella sativa* is disclosed for treating cancer, preventing the side effects of anticancer chemotherapy, and for increasing the immune function in humans.

6 Claims, 2 Drawing Sheets

USE OF *NIGELLA SATIVA* TO INCREASE IMMUNE FUNCTION

FIELD OF THE INVENTION

The present invention is generally directed to the fields of medicine and pharmacology, and specifically directed to using the plant seed extract of *Nigella sativa* Linn (*N. sativa*) in the treatment of cancer, viral diseases, protection from side effects of chemotherapy and growth factor for bone marrow in hematopoiesis.

CITED REFERENCES

A full bibliographic citation of the references cited in this application can be found in the section preceding the claims.

DESCRIPTION OF THE PRIOR ART

A variety of herbal and plant extracts or preparations are available today for treating any number of diseases affecting the human body. Some preparations have been known for literally thousands of years while others are just being discovered to have curative effects. Effective plant extracts are highly desired as a "natural" way to treat a disease. It is believed that natural preparations will not have as much of an adverse effect on the body as synthetic preparations.

One of the primary targets for treatment is cancer. Anticancer remedies are available today which are effective in killing cancer cells. However, many of these medicaments also damage or kill off normal cells or have other serious side effects. It is therefore vitally important to develop an anticancer program which is specific for the cancerous growth in a body, but which is not toxic to the rest of the body system. Ideally, the program will include treatment using natural plant extracts. As used in this disclosure, the term "body" or "patient" can include any warm-blooded mammal, but is specifically intended to refer to the human body.

The medicinal properties of various spices and herbs in general is known (Srivastava, 1989). U.S. Pat. No. 4,986,895 to Grossman et al. is directed to use of water-soluble plant extracts in the treatment of virus skin infections. U.S. Pat. No. 5,178,865 to Ho et al. is directed to the use of Chinese herbal extracts in the treatment of HIV related disease in vitro. A total of 56 herbal extracts were screened for anti-HIV activity using in vitro techniques.

Aruna (1990) also describes the use of spices, leafy vegetables and condiments having diverse medicinal properties. Products of 20 spices or leafy vegetables were screened for anti-carcinogenic activity using induction of glutathione-S-transferase. One of the plants utilized was *Cuminum cyminum* Linn (*C. cyminum*), also known as cumin. All of the spices and leafy vegetables were tolerated well and no toxic effects were seen.

Bitterman et al. (1991) disclose a study that was performed on a population of 964 adult patients, of which 28% suffered from malignant diseases of the urinary tract and 72% from a wide spectrum of the nine neurologic diseases. The results conclude that the use of *C. cyminum* in the diet may contribute to the prevention of diseases mediated by peroxidation of lipids.

Aruna and Sivaramakrishnan (1992) reported on anticarcinogenic properties of some spices. Cumin seeds (*C. cyminum* Linn) were studied. Cumin seed significantly inhibited some carcinogenesis.

Another plant extract from the plant *N. sativa* has shown a wide range of medical use. *N. sativa* is an annual herb belonging to family Ranunculaceae. Other species of Nigella include *Nigela arvensis* and *Nigella damascena*. Induction of callus cultures indicates considerable chromosomal variations in callus tissues between the different species of Nigella (Datta, et al. 1983).

*N. sativa* is characterized by an erect branched stem and alternate finely divided, feathery, grayish-green leaves. The bluish-white, star-shaped flowers are terminal and solitary. Petals are absent. The fruit is a globose capsule with small, black, rough seeds. The plant is cultivated in India, Bangladesh, Turkey, Middle-east and the Mediterranean basin mainly for its seeds or "black cumin" which is almost entirely used for edible and medical purposes, such as spices and for treatment of various diseases.

The ripe seeds of *N. sativa*, also known as Kalajira or Kalaonji, are known to have a wide range of medicinal uses (Kirtikar et al. 1982, and Chopra et al. 1982). The constituents of the seeds include saponin, an essential oil, a bitter compound (nigellone) and tanners. These substances have been shown to have diuretic (Nadkarni 1976), cholagogic and antispasmodic (Tennekoon, et al. 1991), carminative (Shayeb and Mabrouk, 1984), galactogogic (Vihan 1987), antibacterial (Hassan, et al. 1989), antifungal (Agarwal, et al 1979), anthelminthic (Akhtar 1991) and emmenagogic (Siddiqui et al. 1988) properties. al-Awadi, et al. (1985) have demonstrated an antidiabetic effect of *N. sativa* plant extract.

*N. sativa* has been reported to be used in Egyptian folk medicine as a diuretic and carminative (Sayed 1980). The oil is used in the treatment of asthma, respiratory oppression and coughs. The active principle, nigellone, has been isolated from the volatile oil fraction and is reported to be useful in the treatment of bronchial asthma.

The petroleum ether extract of the seeds at 1000–62.5 parts per million (ppm) concentrations was found to have the same activities as growth regulating juvenile hormone when tested against the fifth instar larvae of *Dysdercus similis* (Kumar et al. 1987).

al-Awadi et al. (1981) is directed to the study of the effect of a plant's mixture extract containing *N. sativa* on liver gluconeogenesis. The researchers report that non-insulin dependent diabetes mellitus is treated in Kuwait by a plant mixture extract, which contains *N. sativa*. In this study, a powdered mixture of equal portions of *N. sativa*, Linn, *Commiphora myrrh*, Eng, Ferula Asafoetida, Linn, Aloe vera, Linn, and olibanum was boiled in distilled water for 10 minutes. Diabetic animals were given a daily dose by gastric intubation. The results indicate that the anti-diabetic action of the plant's extract is at least partly mediated through decreased liver gluconeogenesis.

Elkadi and Kandil (1987) are directed to *N. sativa* and its effect on human T-cells. *N. sativa* was tested in volunteers with a low helper T-cell to suppressor T-cell ratio. The results indicated an increase in the helper T-cell population in the experimental group. Further, the helper T-cell to suppressor T-cell ratio increased while the ratio within the control groups remain the same.

Nair et al. (1991) investigated the effects of *N. sativa* as potential protective agents against cisplatin-induced toxicity in mice. Some protective effects were shown by the use of *N. sativa* extracts.

Salomi, N. J., et al. (1992) studied *N. sativa* seeds containing certain fatty acids for antitumor activities against Ehrlich ascites carcinoma (EAC), Dalton's lymphonia ascites (DLA) and Sarcoma-180 (S-180) cells. The paper presents the results of in vitro and in-vivo antitumor experiments. The active antitumor principle was isolated. It was found that the active principle was cytotoxic for EAC cells, KB cells and lymphocytes.

Salomi et al. (1991) reported the effect of the active principle isolated from *N. sativa* in inhibiting chemically induced skin carcinogenesis. Intraperitoneal administration of *N. sativa* extract was shown to prevent the incidents of soft tissues sarcomas and reduced tumor diameters in treated groups.

Metcalf (1984, 1985) reported the inhibitory effects of *N. sativa* on chemical carcinogenesis in mice. However, there was no evidence in these papers of the destruction of human tumor cells.

SUMMARY OF THE INVENTION

The present invention provides an anticancer remedy and treatment which has, as its active ingredient, the extract of the plant *N. sativa*. When used properly, the medicament of the present invention is useful in treating cancer, preventing toxicity of anticancer drugs in human body and in increasing immune function.

The present invention is specifically directed to a pharmaceutical composition for the treatment of cancer comprising a pharmaceutical preparation consisting essentially of an extract from *Nigella sativa*, at a concentration which is effective to destroy cancer cells in a patient.

Additionally, the present invention is directed to a pharmaceutical composition for the treatment of the side effects of anticancer therapy consisting essentially of an extract from *Nigella sativa*, at a concentration of the extract which is effective to reduce the side effects of anticancer therapy.

The present invention is also directed to a method for treating humans suffering from the side effects of anticancer chemotherapy using the extract of *Nigella sativa*, comprising administering to humans effective doses of the composition described above.

Further, the present invention is directed to a method for increasing the immune function in humans comprising administering to humans effective doses of an extract from *Nigella sativa*, at a concentration of the extract which is effective to increase the immune function.

The present invention is also directed to a method for protecting the normal cells from cytopathic effects of virus, comprising administering to humans effective doses of an extract from *Nigella sativa*, at a concentration of the extract which is effective to protect against the cytopathic effects of the virus.

The present invention is still further directed to a method for increasing antibody producing B cells, comprising administering to humans an extract from *Nigella sativa*, at a concentration which is effective to increase the antibody-producing B cells.

The present invention is also directed to a process for inhibiting tumor cells without affecting normal or nontumor cells in a patient comprising administering to a patient an extract from *Nigella sativa*, at a concentration which is effective to inhibit the tumor cells without affecting nontumor cells.

The present invention is also directed to a method for stimulating bone marrow formation in humans comprising administering to humans effective doses of an extract from *Nigella sativa*, at a concentration of the extract which is effective to stimulate bone marrow formation.

In general, *N. sativa* extract helps stimulate bone marrow cells, protects the normal cells from cytopathic effects of virus, destroys tumor cells and increases antibody producing B cells. It protects the bone marrow against chemotherapy and at the same time, can act as an anticancer agent. All these factors makes *N. sativa* seed extract an ideal candidate to be used as vaccine for cancer prevention and cure.

*N. sativa* plant extract is more effective than standard chemotherapeutic anti-cancer drugs. *N. sativa* extract stimulates bone marrow cells, protects the normal cells from cytopathic effects of virus, destroys tumor cells and increases antibody producing B cells. Further, it protects the bone marrow against chemotherapy and can act as an anti-cancer agent.

*N. sativa* plant extract also has been found to help restore immune competent cells in immunosuppressed cancer patients and to overstimulate bone marrow formation in normal individuals.

*N. sativa* extract helps free tumor antigen binding sites on B cells. The administration of the *N. sativa* extract, rather than the increase of the immune competent cell number, has been found to help free tumor antigen binding sites on B cells, thereby elevating the CD19 and associated cell population. When the antigen binding site on the immunoglobulin molecule on the surface of B cells is free because of *N. sativa* treatment, it binds to the tumor associated antigen thereby generating an immune response against the antigen.

Protection of Human Amniotic "WISH" cells from cytopathic effects of vesicular stomatitis virus (VSV) was also observed upon administration of *N. sativa* plant extract. Additionally, the serum interferon level is found to increase; and, hence, the plant extract of *N. sativa* has interferon-like antiviral activity. This is an example of interferon level increasing in the circulation, preventing viral diseases and, in addition, possibly curing viral diseases.

*N. sativa* promotes anti-tumor activity. Data from pharmacosensitivity screening indicates anti-tumor activity of *N. sativa* plant extract mainly against melanoma and colon cancer types. *N. sativa* plant extract destroys tumor cells and leaves normal cells alone, possibly because of its ability to bind to cell surface asialofeutin (lectin) in diseased cells, which causes aggregation and clumping of tumor cells. It also blocks enzymes and inappropriate gene products involved in nucleic acid synthesis and metabolism.

Further objects, features and advantages of the invention will be apparent from the following detailed description when taken in conjunction with the accompanying drawings.

DETAILED DESCRIPTION OF THE INVENTION

Figure 1:
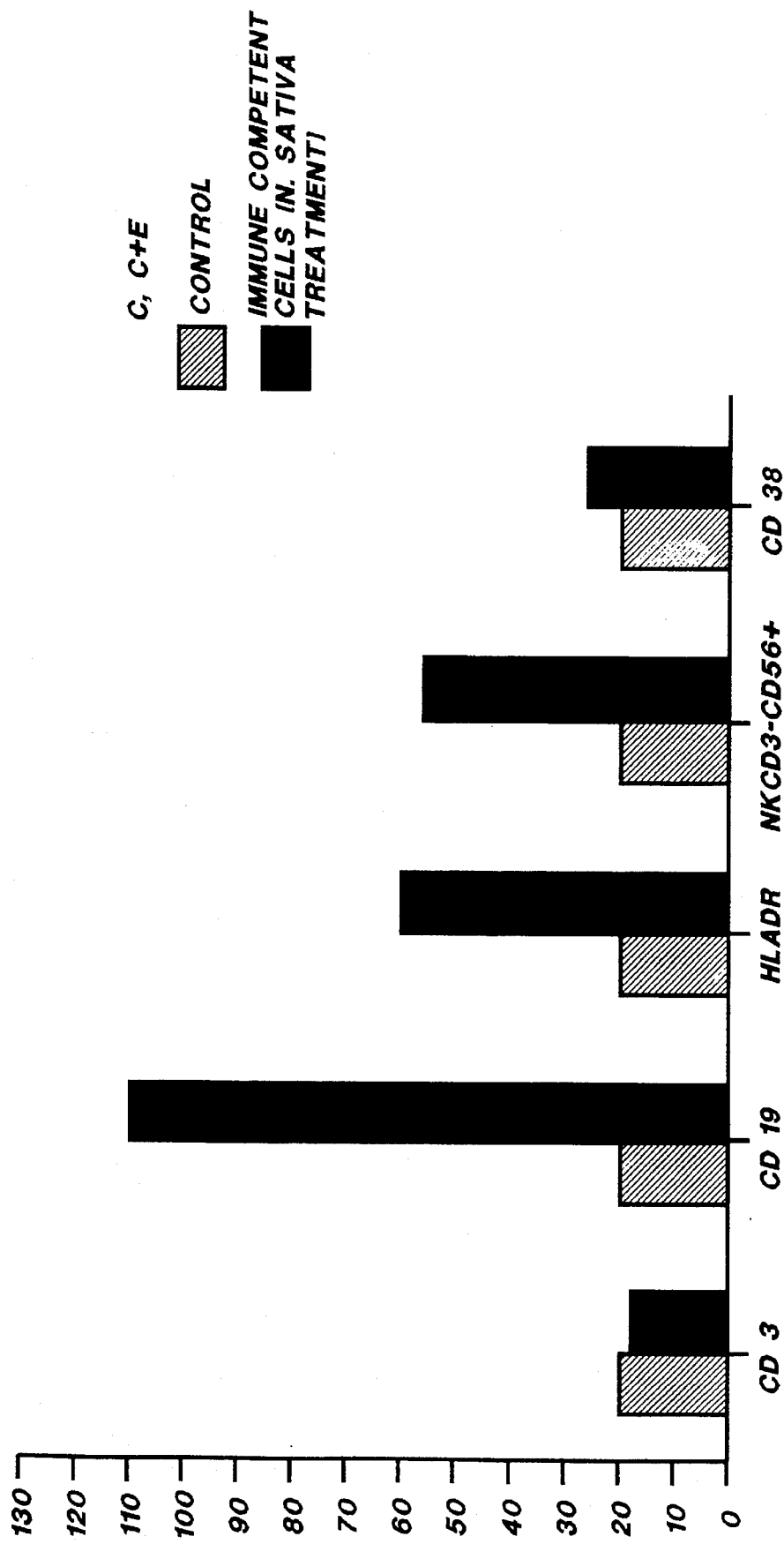
FIG. 1 is a graph illustrating the elevation in CD19, HLADR, NK CD3–/CD56+ and CD38 populations of peripheral blood cells from cancer patients upon incubation with *N. sativa* extract over a 18 hour period at 37° C. in 5% $CO_2$ incubator as shown in Experiment 2.

Definitions:

The following definitions will be used for the present application:

B cells: B cells or B lymphocytes secrete proteins/antibodies that protect the human body against infections.

CD3: Cluster Differentiation 3. These are the antibodies which indicate Activated T lymphocytes which are used by the body for its protection against foreign harmful germs.

CD19: Cluster Differentiation 19. These are antibodies which help detect B lymphocytes. Elevation in CD19 indicates an elevation in B lymphocytes and vice versa.

CD56: Cluster Differentiation 56 are antibodies which inhibit Natural Killer target cell interactions in certain systems.

G-CSF: Granulocyte-Colony Stimulating Factor

GM-CSF: Granulocyte Macrophage-Colony Stimulating Factor.

HLADR: Human Leukocyte antigen DR. DR designates a genetic locus or the antigen of the major histocompatibility complex corresponding to the locus. An increase in HLADR indicates an elevation in immunological parameters against the disease.

NK: Natural Killer cells. NK is an indication to detect the Natural Killer cells.

NKCD3–/CD56+: Natural Killer Cluster Differentiation 3–/Cluster Differentiation 56+.

Preparation of *N. sativa* Extract:

The process for preparing the *N. sativa* extract comprises grinding the seeds and separating the extract of the *N. sativa* with appropriate solvents such as alcohol or water, removing lipids by extraction with ether or petroleum ether, crystallization or chromatographic fractionation and then mixing its components in the desired proportion. The *N. sativa* extract can then be prepared in 3 forms—oil, fluid and crystal—by processes known to the art. The preferred process for the preparation of *N. sativa* extract is described in Experiment 1.

Administration:

The extract of *N. sativa* may be administered by itself or in admixture with an appropriate excipient or carrier. The preparation may be administered to the patient by enteral, such as oral or rectal, and parenteral, such as intraperitoneal, intramuscular, intravenous or subcutaneous route. The preparation may also be administered in combination with supplements, such as antiviral agents, immune modulators, antibodies, other chemotherapeutic agents, or combinations thereof. The preparation may additionally be administered in dosage form, such as by capsules, tablets, suppositories or the like.

Dosages:

*N. sativa* has been found to be most effective when administered at a dosage of 30 g per day, with an effective range of 20–40 g per day.

*N. sativa* extract is also known to confer protection of human amniotic "WISH" cells against cytopathic effects of vesicular stomatitis virus (VSV). The plant extract at a dilution of 1:1000 when incubated with $3.5 \times 10^4$ WISH cells for 18 to 24 hours at 37° centigrade gave maximum protection.

Theoretically, a patient weighing 70 kg has about $7 \times 10^{13}$ cells in its body and *N. sativa* will be useful at a dosage between about 20 and 40 g per day and preferably about 30 g per day to protect against viral attack in virus endemic areas.

The invention is further illustrated by the following experiments and tests but not limited by the following experiments:

EXPERIMENTS

To evaluate the usefulness of *N. sativa* for cancer treatment, the activity of the *N. sativa* extract was measured on bone marrow and peripheral white blood cells. In vitro antiviral antitumor and growth factor like activity were also measured.

*N. sativa* extract was incubated with bone marrow cells to determine the growth of the cells. The results were compared with that of bone marrow growth factors and biological response modifiers (GM-CSF, G-CSF, erythropoietin, interferon, IL-2, and STS). Mouse connective cells and human amnion or "WISH" cells were also assayed.

The following calculations were used in the examples:

Calculation of Percent Elevation:

Formula:
$$\% \text{ elevation} = 1 - \frac{R_T - R_C}{R_{MAX} - R_C} \times 100$$

in which $R_T$ is the average cell count of the experimental well with extract/growth factors, $R_C$ is the average background cell count with control, $R_{MAX}$ is the average maximum elevation without extract/growth factor.

Calculation of Percent Inhibition:

Formula:
$$\% \text{ inhibition} = 1 - \frac{R_T - R_C}{R_{MAX} - R_C} \times 100$$

in which $R_T$ is the average cell count of the experimental well with extract/Abrin control, $R_C$ is the average background cell count with control, $R_{MAX}$ is the average maximum inhibition without extract/Abrin control.

Following are descriptions of some procedures used in the experiments. Universal safety precautions, known to the art, must be observed when handling all biological materials.

Procedure 1

Flow Cytometry Direct Immunofluorescence Staining

Automated Flow Cytometry (FC) provides an efficient, sensitive and quantitative method to analyze cell populations, sub-populations, and their components in suspension. Cells express and shed surface antigens throughout their life indicating their classification, stage of maturation, activation state and disease state. Monoclonal antibodies (mABs) have been developed that specifically bind these surface antigens. Established clinical applications are in leukemia and lymphoma diagnosis, T-cell subset analysis, monitoring transplant rejection, monitoring the effects of chemotherapeutic agents on different cell types and measuring cellular activation.

Whole blood, bone marrow or cellular suspension is first treated with a red blood cell lysing solution, washed, and then mixed with a labeled mAB against a specific membrane antigen. The direct staining procedure is then followed by analysis with the FACSCAN Immunocytometry Systems flow cytometer (FACSCAN Users' Guide, Becton Dickinson).

All specimens are generally labeled with the following information: 1) Patient name; 2) Date drawn; 3) Time drawn; 4) Phlebotomist's initials; and 5) Panel number. Patient specimens are identified by the nurse or phlebotomist generally by checking the wristband to verify the name of the patient. A unique tracking number is assigned to each individual specimen to assure proper specimen tracking.

Peripheral Blood is aseptically collected in an appropriate container such as a lavender top (EDTA anti-coagulant) vacutainer tube and delivered at room temperature preferably within 48 hours. The minimum amount required is approximately 2 ml whole blood per panel ordered. The optimum amount required is approximately 3 ml whole blood per panel ordered The bone marrow (BM) specimen is aseptically collected in a container such as a lavender top (EDTA) vacutainer tube and transported at room temperature within 48 hours. The minimum amount required is approximately 2 ml of BM specimen per panel ordered. The optimum amount is approximately 3 ml of BM specimen per panel ordered.

Solid tumors include those from the breast, lymph node, colon, ovarian, lung, and skin. Reference is made to the HTCA Pharmacosensitivity Procedure (Procedure 5, infra.) for a description of the procedures. The tumor should be delivered at room temperature within 48 hours of extraction. The minimum amount required is approximately 2 ml of cells at a concentration of $1\times 10^6$/ml per panel ordered. The optimum amount is approximately 3 ml of cells at a concentration of $1\times 10^6$/ml per panel ordered.

Materials:

The materials required are as follows:

EDTA Vacutainer Blood Collection Tubes

12×75 mm plastic test tubes

Serofuge

FACSCAN Flow Cytometer

Micropipettes (20 ul and 100 ul)

Micropipet Tips

Repeater Pipet

Small Beakers

Gauze Squares

Monoclonal Antibodies

Lysing Solution

PBS 0.5% p-Formaldehyde

Transport Media 50 ml Conical Tubes

Repeater Pipet Tips

Safety Shield

Sorvall TR6000 centrifuge

Coulter Cytotrol control cells

Reagents:

The reagents are prepared as follows:

A. Monoclonal antibodies—see package inserts for proper reconstitution and storage of various mABs. For Coulter mABs, reconstitute according to package insert and then make a 1:2 dilution in sterile water and place in an appropriate container.

B. Lysing solution—(Becton-Dickinson order #92-0002). To prepare 1× working solution, add 10 ml 10× lysing stock solution to 90 ml distilled water. Mix well. Store at room temperature. Discard after one week.

C. Phosphate Buffered Saline (PBS) without Ca++ and Mg++ (Gibco order #310-4190AJ)

D. 0.5% Paraformaldehyde. Dissolve 2.5 g paraformaldehyde (Baker S-898-7) in 500 ml of 1× PBS without Ca++ or Mg++.

E. Coulter Cytotrol control cells. Reconstitute Cytotrol control cells according to manufacturers' package insert. These cells must be prepared fresh daily.

Quality Control:

A leukogate and a negative control tube must be run for each patient. Tubes for Cytotrol control cells should be included for each mAB used that day.

Procedure:

Label test tubes with patient name and appropriate mAB. Using a micropipet, to each tube add 20 ul of the appropriate antibody. Using a micropipet, to each tube add 100 ul of the patient whole blood. Vortex each tube. Incubate the tubes at room temperature for 15 minutes. Using the repeater pipet (set on 4) add 2 ml of 1× lysing solution to each tube. Incubate the tubes at room temperature for 10 minutes. Centrifuge tubes in serofuge set on high for 3 minutes or in Sorvall TR6000 for 5 minutes at 3000 RPM. Pour off supernatant in waste beaker, being careful not to splash. Blot top of tube on gauze square. Vortex each tube to break pellet (use safety shield). Using repeater pipet (set on 4) add 1 ml of 1× PBS to each tube and vortex each tube (use safety shield). Centrifuge tubes in a serofuge set on high for 3 minutes .or in Sorvall TR6000 for 5 minutes at 3000 RPM. Pour off supernatant in waste beaker being careful not to splash. Blot top of tube on gauze square. Vortex tubes to break pellet (use safety shield). Using repeater pipet (set on 2) add 0.5 ml of 0.5% paraformaldehyde. Vortex. Keep tubes covered with parafilm and in the refrigerator until ready for flow cytometric analysis.

Specimen Analysis:

Analyze each tube on the FACSCAN flow cytometer using Simulset software for surface marker evaluation. (Refer to FACSCAN Users' Guide and Simulset Software Manual.) Use the complete blood count (CBC) information (be sure CBC was drawn same date and time as FC sample) to enter the total white blood count and % lymphocytes.

Procedure 2

Colony Forming Cells

In order to be able to calculate the potency of the bone marrow, the stem cell assay is performed. Information on the status of Colony Forming Units (CFU) before therapy is performed is obtained. This will allow one to precisely define the medication according to the possible toxicities developed. Also, this will allow the prediction of the toxicity of the medication. The character of CFU when stem cells are treated with different medications will help determine predominance of development of cell lines. It has been demonstrated that interferon prolongs myelopoietic differentiation; therefore, the number of CFU will increase. This will demonstrate efficiency of interferon on bone marrow recovery and confirm the protective activity of interferon to the bone marrow.

With different hemopoietic growth factors, CFU development for the different cell lines can be directed.

Specimen Requirements, Collection and Handling:

Specimen Requirements: Bone marrow sufficient to yield a minimum of 4.0 ml and an optimum of 5.0 ml mononuclear cells at a concentration of $1.0\times 10^6$ cells/ml.

Bone Marrow collection procedure: Prepare 4-6 50 ml Falcon tubes containing 20 ml of tissue transport media. Transport the media in the cooler with frozen ice chips to the procedure. A mask, gloves and gown must be worn during the procedure. Inject 2500 units of preservative-free heparin into the media tubes using sterile technique. This must be done no earlier then 15 minutes before obtaining the bone marrow specimen. Mix well. When bone marrow is handed to the technologist in a syringe, carefully inject into the media tubes, rinsing with media twice. Discard syringe in the Sharps container. Cap tube and mix well. Label the specimen with the following: 1) Patient's full name; 2) Date specimen was received; 3) Time specimen was received; and 4) Initials of technologist who obtained the specimen. Place in cooler with ice chips for transportation.

Materials:

The following materials are necessary:

Ficoll-Hypaque

Capped Test Tubes [Sterile] 15 ml

Falcon Tubes-50 ml

Sterile Laminar Flow Hood with UV Light

Centrifuge

Sterile Disposable Pipettes
  1.0 ml
  5.0 ml
  10.0 ml
  25.0 ml

RPMI 1640 [1×]

Iscove's Modified Dulbecco's Medium [1×]

Fetal Bovine Serum

Penicillin/Streptomycin

L-Glutamine [100×]

Trace Elements [100×]

2-Mercaptoethanol

Insulin Transferrin-Sodium Selenite Media Supplement (ITS)

Glass Test Tubes 12×75 ml

Trypan Blue Stain (0.4%)

Hemocytometer With Cover Slips

Microscopes (Light, Inverted)

Tissue Culture Flasks-25 $CM^2$

Somatostatin-50 µg/ml (Sandoz-Sandostatin)

Interferon-3×$10^6$ U/ml (Roferon A-Hoffman LaRoche)

Interleukin-2 (Boehringer Mannheim GMBH Cat #799068)

GM-CSF (Amgen Cat #13050)

G-CSF (Amgen Cat #10050)

Epogen (Amgen Cat #06050)

PIXY 321 (Immunex)

$CO_2$ Incubator

Hand Counter

Ice Chips

Media and Reagent Preparation:

After preparation of each media, the final product is labeled with the following: 1) Name of Product; 2) Preparation Date; 3) Expiration Date; 4) Storage Recommendations; and 5) Technologist's Initials. 10% RPMI 1640 (1×) G,G Fortified:

| AMOUNT | COMPONENT |
|---|---|
| 500.0 ml | RPMI 1640 (1X) with L-Glutamine |
| 50.0 ml | Fetal Bovine Serum (Qualified, Heat Inactivated) |
| 5.0 ml | L-Glutamine (100X), 200 mM |
| 1.5 ml | Penicillin/Streptomycin |
| 2.0 ml | Trace Element Mix (100X), Lyophilized |
| 0.5 ml | 2-Mercaptoethanol |
| 5.0 ml | ITS Media Supplement, Lophilized, |

| AMOUNT | COMPONENT |
|---|---|
| | Gamma-Irradiated |

All components are combined under a sterile laminar flow hood, and sterilized by filtration using a 0.22 micron membrane filter with a 60 micron prefilter. The prepared media is labeled and stored at 2°–10° C.

IMDM/RMPI 1640 [1×] (Tissue Transport Media):

| AMOUNT | COMPONENT |
|---|---|
| 500.0 ml | RPMI 1640 [1X] |
| 500.0 ml | IMDM [1X] |
| 100.0 ml | FBS |
| 5.0 ml | Penicillin/Streptomycin |
| 10.0 ml | L-Glutamine (100X) |
| 5.0 ml | Trace Element Mix (100X) |
| 5.0 ml | Nonessential Amino Acids (100X) |
| 0.5 ml | MEM Vitamins |
| 0.5 ml | 2-Mercaptoethanol |
| 5.0 ml | ITS |

All components are combined under a sterile laminar flow hood, and sterilized by filtration using a 0.22 micron membrane filter with a 60 micron prefilter. The prepared media is labeled and stored at 2°–10° C.

Interferon:

Use 1 vial of Roferon A Interferon available from Hoffmann-LaRoche Inc. (3,000,000 U). Take 1 ml Interferon and add 39 ml of RPMI(1×) media to yield a concentration of 75,000 U/ml. Make 40 1 ml aliquots of this dilution and freeze. For the Colony Forming Assay use 1 ml of the 75,000 U/ml Interferon for each 25 $cm^2$ flask containing 4.0 ml of media and 0.5 ml of cells.

Interleukin-2:

Thaw interleukin-2 and take 5 ml of interleukin-2 containing 200 units per ml. Immediately freeze remaining interleukin-2 into 5 ml aliquots. Add 5 ml of RPMI(1×) media to 5 ml of interleukin-2 containing 200 units per ml to obtain a concentration of 100 units/ml. To 10 tubes containing 9 ml of the media, add 1 ml of interleukin-2 at a concentration of 100 units/ml to obtain a concentration of 10 units/ml. These aliquots are stable for 30 days at 4°–8° C. For colony forming assay, use 0.5 ml (or 5 units) for each 25 $cm^2$ flask containing 4.5 ml of medium and 0.5 ml of cells.

Somatostatin:

Somatostatin is available in single vials containing 50 µg/ml and 100 µg/ml from Sandoz Ltd. Store at 4°–8° C. For the Colony Forming Assay, use 1.0 ml of STS containing 50 µ/ml for each 25 $cm_2$ flask containing 4.0 ml of media and 0.5 ml of cells. This procedure is written for 50 µg/ml vials. If 100 µg/ml vials are used, use 0.5 ml of Somatostatin and 4.5 ml of media for a 25 $cm^2$ flask.

GM-CSF:

Dilute 250 ul of GM-CSF containing 50,000 units in 50 ml of media to obtain 1000 units/ml. Prepare aliquots of 5 ml each containing 5,000 units in sterile tubes with caps. Label each aliquot: GM-CSF—5,000 units (1,000 units/ml). Close nine of these aliquots with sterile adhesive and store at 4° C. Aliquot #10, containing 1,000 units/ml (total 5,000 units), will be used as follows: Pipet one ml into each of 5 sterile tubes. Add 19 ml of media to obtain 50 units/ml. (Each tube will contain a total of 1,000 units). Label each of these aliquots: GM-CSF—50 units/ml (total 1,000 units).

Close 4 of these aliquots with sterile adhesive and store at 4° C. Aliquot #5 will be marked "IN USE" and stored at 4° C. For colony forming assay, use 50 ul (or 2.5 units) for 25 cm² flask containing 5.0 ml of medium and 0.5 ml of cells.

G-CSF:

Dilute 125 ul of G-CSF, containing 60,000 units in 50 ml of media to obtain 1200 units/ml. Prepare aliquots of 5 ml each containing 6,000 units in sterile tubes with caps. Label each aliquot: G-CSF—6,000 units (1,200 units/ml). Add the date. Close 9 of these aliquots with sterile adhesive and store at 4° C. Aliquot #10 containing 5 ml of 1,200 units/ml (total 6,000 units), will be used as follows: Pipet one ml into each of 5 sterile tubes. Add 19 ml of media to obtain 60 units/ml (each tube will contain a total of 1,200 units). Label each of these aliquots: G-CSF—60 units/ml (total 1,200 units). Add the date. Close 4 of these aliquots with sterile adhesive and store at 4° C. Aliquot #5 will be marked "IN USE" and stored at 4° C. For colony forming assay, use 50 µl (or 3 units) for each 25 cm² flask containing 5.0 ml of media and 0.5 ml of cells.

Epogen:

To one ml of epogen containing 2,000 units, add 19 ml of media to yield 20 ml of 2,000 units or 100 units/ml. Aliquot 2 ml into each of 10 cryovials. Label as follows: Epogen—100 units/ml and date. Store at 4°–8° C. For colony forming assay, use 50 µl (or 5 units) for each 25 cm² flask containing 5.0 ml of medium and 0.5 ml of cells.

PIXY 321-GM-CSF/IL-3:

Using 15 ml sterile capped tubes, dilute 1 ml of Pixy 321 (be sure to quantitatively transfer by rinsing vials) with 9 ml of 10% BSA and mix well. This will yield a neutralizing effect of $1.0 \times 10^6$ units/ml. Aliquot 1.0 ml of this solution of $1 \times 10^6$ units/ml into each of 9 cryovials. Label each vial with: name, concentration and expiration date. Store at $-70°$ C. To the remaining 1 ml of $1.0 \times 10^6$ units/ml, add 9 ml of 10% BSA and mix well. This will yield a neutralizing effect of $1.0 \times 10^5$ units/ml. Aliquot 1.0 ml of this solution of $1 \times 10^5$ units/ml into each of 9 cryovials. Label each vial with: name, concentration and expiration date. Store at $-70°$ C. To the remaining 1 ml of $1.0 \times 10^5$ units/ml, add 9 ml of 10% BSA and mix well. This will yield a neutralizing effect of $1.0 \times 10^4$ units/ml. Aliquot 1.0 ml of this solution of $1 \times 10^4$ units/ml into each of 9 cryovials. Label each with: name, concentration, and expiration date. Store at 70° C. To the remaining 1 ml of $1.0 \times 10^4$ units/ml, add 9 ml of 10% BSA and mfx well. This will yield a neutralizing effect of $1.0 \times 10^3$ units/ml. Aliquot 1.0 ml of this solution into each of 10 cryovials. Label each with: name, "Working Pixy," concentration, and expiration date. Store at $-70°$ C. One vial may be thawed and stored at 4° C. for use in the assay. Take 1 ml aliquot of $1.0 \times 10^3$ units/ml out of the $-70°$ C. freezer and thaw. This will be marked "in use" and stored at 4° C. For Colony Forming Assay, use 50 µL (or 2.5 units) for 25 cm² flask.

PROCEDURE

Sample Processing:

Using a sterile pipet, dispense 20–25 ml of histopaque into the appropriate number of capped sterile 50 ml conical tubes. Using another sterile pipet, gently layer the bone marrow at a 45° C. angle onto the histopaque using a 1:1 ratio of histopaque to specimen. Centrifuge at 1600 RPM for 20 minutes in refrigerated centrifuge at 4° C. (brake on 2). Remove and discard the supernatant. Remove the cell interface and place in RPMI(1×) in a pre-labeled tube. Wash cells twice with RPMI(1×) media and centrifuge at 1600 RPM for 5 minutes with a brake of 2. Remove and discard the supernatant. Resuspend the cell pellet in 5 ml of RPMI(1×) medium.

Perform cell count:

In a 12×75 ml glass tube, combine:

0.1 ml of well-mixed cell suspension 0.2 ml of 0.4% Trypan Blue stain 0.7 ml of media This is a 1:10 dilution.

Mix well and charge one chamber of the hemocytometer with the cell suspension. Under the light microscope, count the viable cells (those which have not absorbed the Trypan Blue) in the four corner 1 mm² squares. Count the total number of cells (stained and unstained) in the four corner 1 mm² squares.

Calculation for Cell Concentration:

1. Perform the viable cell count using the following equation:

Average number of viable cells per square× dilution factor×hemacytometer factor =cells/ml Sample calculation: 20 Cells (average # of viable cells per square)×$10^4$×10 (dilution factor)=2× $10^6$ cells/ml.

2. Determine the % viability using the following formula:

Viable cell count×100=% viability total cell count

3. Adjust volume to amount needed for the appropriate cell concentration for the assay (this assay requires $1 \times 10^6$ cells/ml) using the following formula:

$(V_1 C_1 = V_2 C_2)$

For example:

$V_1 = 10$ ml $V_2 = ?$ $C_1 = 2 \times 10^6$ cells/ml $C_2 = 1 \times 10^6$ cells/ml $$\frac{V_1 C_1}{C_2} = V_2$$

10 ml×2×$10^6$ cells/ml=$V_2$ $1 \times 10^6$ cells/ml 20 ml=$V_2$ 20 ml–10 ml=10 ml Ten ml of media must be added to have a volume of $1 \times 10^6$ cells/ml.

4. Prepare the flasks: label eight 25 cm² liquid tissue culture flasks with the following information: 1) Patient name; 2) Tracking number; 3) Date; 4) Growth Factor or BRM.

5. To each of the 25 cm² flasks, add bone marrow cells (BMC), growth factor or biological response modifier (BRM), and media according to Table 1:

TABLE 1

|  | Growth Factor | | |
| --- | --- | --- | --- |
|  | BMC | BRM | Media |
| BMC + M (Control) | 0.5 ml | — | 5.0 ml |
| BMC + IFN + M | 0.5 ml | 1.0 ml | 4.0 ml |
| BMC + IL2 + M | 0.5 ml | 0.5 ml | 4.5 ml |
| BMC + STS + M | 0.5 ml | 1.0 ml | 4.0 ml |
| BMC + GM-CSF + M | 0.5 ml | 50 µl | 5.0 ml |
| BMC + G-CSF + M | 0.5 ml | 50 µl | 5.0 ml |

TABLE 1-continued

|  | Growth Factor | | |
| --- | --- | --- | --- |
|  | BMC | BRM | Media |
| BMC + EPO + M | 0.5 ml | 50 µl | 5.0 ml |
| BMC + PIXY + M | 0.5 ml | 50 µl | 5.0 ml |

NOTE:
The final volume in all flasks will be 5.5 ml.

NOTE: The final volume in all flasks will be 5.5 ml.

6. Incubate the flasks in the 37° C. and 5% $CO_2$ incubator. The flasks are to be read and fed as needed, taking care to treat each flask in the assay the same.

Reading and Reporting Results:

At days 7, 14 and 21, scan each of the flasks of the colony forming assay for colonies under the inverted microscope. A colony is defined as 40 or more cells adhering to the bottom of the flask. Floating colonies are not to be counted. Scan the entire flask and report the total number of colonies counted for each flask on the colony forming assay report form.

If no growth is seen at the end of 21 days, report as "No Growth" and hold the flasks for an additional 7 days. Flasks may be discarded after the final report is reviewed by the Medical Director.

Procedure 3

Immunomodulatory Testing

The prediction of clinical or in vitro response to cancer therapy and the corresponding determination of optimum patient treatment through the use of in vitro assays has been the goal of many investigators. The immunomodulatory assay is a procedure to determine how the patient will react to certain biological response modifiers in vitro. It is a necessary addition to other forms of testing in that it can determine if a patient's serum naturally contains the factors which are able to suppress or activate the growth of tumor cells.

In this procedure, the patient's serum, and/or WBC's, is combined with various biological response modifiers (BRM) and co-cultured with a tumor cell line. The percentage of stimulation or percentage of inhibition of the tumor cell growth is determined. This information enables the oncologist to determine appropriate and customized treatment for each patient.

SPECIMEN REQUIREMENTS AND COLLECTION

Label all specimens with patient name, date drawn, time drawn, and phlebotomist's initial. A unique tracking number will be assigned to each individual specimen to assure proper specimen tracking.

Requirements:
1. Whole blood (WB)—10 ml
2. Serum—3 ml
3. Bone Marrow (BM)—one BM aspiration in 25 ml of transport media. The optimum amount is 3 ml at $1 \times 10^6$ cells per ml.
4. Plasmapheresis specimen—3 ml Both a whole blood specimen and a serum specimen are required for complete immunomodulatory evaluation. However, in the event that only one of the two specimens (WB or serum) is available, partial immunomodulatory testing may be performed.

Collection, Processing, and Handling:

The patient will be properly identified by the nurse or phlebotomist (i.e., check wristband, verify patient name).

Specimens will be aseptically collected by the nurse or a phlebotomist. Gloves and lab coat must be worn while drawing or handling the specimen and "universal precautions" must be observed.

1. Whole Blood a. Collection—Add 2500 units of preservative free heparin (Calciparine) to a 10 ml red top vacutainer tube. Perform venipuncture and draw the patient's blood into tube. Label all tubes with patient's name, date and time collected. Invert several times to mix anticoagulant. Refrigerate tube until ready for separation of the mononuclear layer by the density gradient procedure (Reference is made to Procedure 4, infra., at part B-2).

Minimum amount whole blood=7 ml

Optimum amount whole blood=10 ml b. Unacceptable Specimens—Clotted specimens, grossly hemolyzed specimens, or frozen specimens are unacceptable.

c. Rejection of Specimens—When any criteria are not met, the unacceptable specimens may be tested if necessary.

2. Serum a. Collection—Use a red top vacutainer tube to perform venipuncture and draw 10 ml of the patient's blood into the tube. Centrifuge the serum specimen at 2000 RPM for 10 minutes at 25° C. Refrigerate tube until testing. Aseptically draw off serum and place in a separate tube.

Minimum amount serum=3 ml

Optimum amount serum=5 ml b. Unacceptable Specimens—Specimens with excessive fibrin clotting are unacceptable.

c. Rejection of Specimens—When any criteria are not met, the unacceptable specimens may be tested if necessary.

3. Plasmapheresis a. Collection—Add 2500 units of preservative free heparin (Calciparine) to a 10 ml red top vacutainer tube. Draw from the plasma collection container at the beginning of the plasmapheresis procedure. Label tube #1. Refrigerate until testing. Minimum amount of plasma=3 ml Optimum amount of plasma=5 ml b. Unacceptable Specimens—Specimens with excessive fibrin clotting are unacceptable.

c. Rejection of Specimens—When any criteria are not met, the unacceptable specimens may be tested if necessary.

4. Bone Marrow a. Collection—Not more than 15 minutes prior to the BM procedure, add 2500 units of Calciparine per 25 ml of tissue transport media using aseptic techniques. Using aseptic techniques, quickly add the BM specimens to the transport tube and mix well. Refrigerate the tube until ready for separation of the mononuclear layer by the density gradient procedure (see part IV, section B-2).

b. Unacceptable Specimens—Grossly clotted specimens, grossly hemolyzed specimens, or frozen specimens are unacceptable.

c. Rejection of Specimens—When any criteria are not met, the unacceptable specimens may be tested if necessary.

MATERIALS:

The following materials are required for this procedure:

Laminar Flow Hood

Bacto-Agar

Balance

Weighing Paper
Weighing Tools
Capped Bottles (Sterile) (−250 ml, −500 ml)
Distilled Water (Sterile)
Microwave Oven
Autoclave
RPMI 1640 Media
Gentamicin
Disposable Pipettes (Sterile) (−1 ml, −2 ml, −5 ml, −10 ml, −25 ml)
Glutamine
Trace Elements
2-Mercaptoethanol with Dulbecco's PBS
ITS Solution
Fetal Bovine Serum
Test Tubes (Capped) (−5 ml, −10 ml)
Petri Dishes (Sterile) (Regular 100×15 mm, Gridded 35 mm)
Falcon Tubes
Conical Tube (Sterile-Plastic)
Trypan Blue Stain (0.4~)
Hemocytometer with Cover Slips
Microscopes (Tissue Culture Inverted Microscope, Light Microscope)
pH Paper (Narrow Spectrum)
Graduated Cylinders (50 ml, 100 ml)
Histopaque-1077
Water Bath
Suction Pipetter
Refrigerated Centrifuge
$CO_2$ Incubator
Biological Response Modifiers (Recombinant Interferon Alpha 2a, Recombinant Interleukin-2, mAB to Interferon Alpha)
Vortex Mixer
Refrigerator (2–8 C.)
Hand Counter
Sharps Container
Pasteur Pipettes
Dropper Bulbs
−70° C. Freezer
Precise Surface Disinfectant
Micro Glassware Disinfectant/Cleanser
Beaker (250 ml)
Betadine Disinfecting Solution
Syringes (1 cc) (Sterile)
Needles (Various Gauges)
Vacutainer Tubes (Red Tops and "Tiger Tops")

MEDIA AND REAGENT PREPARATION

Prepare Agar:
Lower layer (2.5% working solution): Weigh out 2.50 gm of Bacto-Agar and place in a 100 ml capped bottle. Add 100 ml distilled water. Swirl gently to mix.
Upper layer (1.5% working solution): Weigh out 1.50 gm of Bacto-Agar and place in a 100 ml capped bottle. Add 100 ml distilled water. Swirl gently to mix. Place both bottles in the microwave with caps loosened. Microwave for 60 seconds at full power, mixing every 20 seconds. Avoid boiling. The agar will appear clear when ready. If solution boils over, do not use it. Re-make the agar solution. Loosely tape cap with autoclave indicator tape and autoclave both solutions for 20 minutes at 22 psi and 250°–270° F. Place both bottles in the water bath under the hood. This bath must be kept at 45°–50° C. at all times. The agar should cool down to 50° C. before use. Swirl agar to mix well before using.

Prepare Media:
After preparation of each media, label the final product with the following: 1) Name of Product; 2) Preparation Date; 3) Expiration Date; 4) Storage Recommendations; 5) Technologist's Initials 10% RPMI 1640 (1×) G,G fortified:

| AMOUNT | COMPONENT |
| --- | --- |
| 500.0 ml | RPMI 1640 (1X) with L-Glutamine |
| 50.0 ml | Fetal Bovine Serum, Qualified, Heat Inactivated |
| 5.0 ml | L-Glutamine (100X) 200 mM |
| 2.5 ml | Penicillin/Streptomycin |
| 2.0 ml | Trace Element Mix (100X), Lyophilized |
| 0.5 ml | 2-Mercaptoethanol |
| 5.0 ml | Insulin-Transferrin-Sodium Selenite, Media Supplement, Lyophilized, Gamma-Irradiated |

Combine all components under a sterile laminar flow hood. Sterilize by filtration using a 0.22 micron cellulose acetate membrane filter with a 60 micron prefilter. Store the prepared media at 2°–10° C.

10% RPMI 1640 (2×) G,G Fortified:

| AMOUNT | COMPONENT |
| --- | --- |
| 500.0 ml | RPMI 1640 (2X) Powdered Cell Culture Medium with L-Glutamine (Reconstitute one powder pack with a total of 500.0 ml of sterile distilled water) |
| 50.0 ml | Fetal Bovine Serum, Qualified, Heat Inactivated |
| 5.0 ml | L-Glutamine (100X) 200 mM |
| 2.5 ml | Penicillin/Streptomycin |
| 2.0 ml | Trace Element Mix (100X), Lyophilized |
| 0.5 ml | 2-Mercaptoethanol |
| 5.0 ml | Insulin-Transferrin-Sodium Selenite, Media Supplement, Lyophilized, Gamma-Irradiated |

Under a sterile laminar flow hood, measure out 450 ml of sterile distilled water and place in a sterile 500 ml reagent bottle. Add the powdered medium to the water with gentle stirring. Rinse out the inside of the package to remove all traces of powder. Add 1.0 g of $NaHCO_3$ per 500 ml of medium. Dilute with sterile distilled water to 500 ml. Adjust the pH of the preparation to 0.2–0.3 below the desired final working pH (pH units will usually rise 0.1–0.3 upon filtration); use of 1N NaOH or 1N HCl is recommended. After the pH has been adjusted, keep the container closed until the medium is filtered. Sterilize immediately by membrane filtration using a 0.22 micron cellulose acetate membrane filter with a 60 micron prefilter. Store the prepared media at 2°–10° C.

Prepare Lower Layer Stock Media:

| | |
|---|---|
| 125 ml | Fetal Bovine Serum |
| 125 ml | 2 × G, G Fortified Solution |
| 250 ml | 1 × G, G Fortified Solution |

Mix, label, and store at 2–10° C.
Prepare Upper Layer Stock Media:

| | |
|---|---|
| 150 ml | Fetal Bovine Serum |
| 150 ml | 2 × G, G Fortified Solution |
| 150 ml | 1 × G, G Fortified Solution |

Preparation of Drugs:
Prepare a working concentration for the drugs to be tested. All drug dilutions are made with RPMI 1640 1× G,G Fortified.

To prepare IFN Alpha-2a in a 10 ml capped tube, mix 0.1 ml Roferon (3,000,000 units/ml) with 9.9 ml 1× G,G, Media. Label tube with name of drug, preparation date, expiration date (1 week from the day of preparation), concentration (30,000 u/ml) and technician's initials.

To prepare IL-2 in 10 ml capped tube: Remove working stock aliquot of IL-2 (10 units/ml) from refrigerator. If the aliquot is not available in refrigerator, follow the IL-2 aliquot procedure found in the aliquot procedure book. The stock tubes are kept in the −48° C. freezer. The dosage for testing will be 0.1 ml, which will equal 1 unit of interleukin-2. Therefore, 1 unit of interleukin-2 will be tested in the immunomodulatory procedure. Interleukin-2, in this media, can be maintained for 30 days at 2°–8° C.

To prepare LI-8-ABIFN (mAB to IFN alpha 2A) in a 10 ml capped tube, remove working aliquot (neutralizing effect of 1000 units/ml from freezer). The dosage will be 0.1 ml in the assay to achieve a concentration of 100 units of neutralizing ABIFN.

PROCEDURE:
Lower Layer (2.5% agar):
Use lower layer stock media and dispense 8 ml of stock media into the appropriate number of sterile 15 ml tubes with caps. (Approximately 8 plates can be made from 1 tube.) Keep capped at room temperature until needed to prepare lower layer plates or store capped overnight at 2°–8° C. for use the following day. Warm to room temperature before use. When ready to prepare the lower layer plates work quickly to prevent premature solidification of the agar. Using a sterile 10 ml pipet draw up 2.0 ml of the 2.5% agar mixture. Dispense the 2.0 ml into one of the 15.0 ml plastic tubes containing 8 ml of lower layer media, and mix twice by drawing up and dispensing into the tube. Draw up 9.0 ml of the mixture and dispense 1.0 ml into each 35 mm gridded plate. Swirl to cover the bottom of the plate. Take care to prevent bubbles. Prepare only 8 plates at a time so that the agar does not solidify before it is plated. Allow plates to sit undisturbed on a flat surface until the agar has solidified. Discard any plates with uneven agar distribution. Store plates at room temperature for same day use or overnight in a 37° C. CO2 incubator for use the following day.

Preparing the Cells Lines:
Generally, L929 cells are used in the assay, but colon, prostate, breast or ovarian cells may also be used.

For L929 cells, microscopically examine the liquid culture flasks of the desired cell line and determine by confluency which flasks to use. Remove supernatant with pipet and discard. Add 5 ml Trypsin. Expose to cell layer and remove 2 ml. Incubate flasks with Trypsin for minute. Hit flask with the palm of your hand to knock cells off. Add 7 ml of L929 cell media to stop reaction. Transfer cells to a sterile 50 ml conical tube, add more media (to bring to 20 ml). Centrifuge tube @ 1600 RPM for 5 minutes with brake on 2. Remove supernatant and resuspend pellet in L929 cell media. Centrifuge cells at 1600 RPM for 5 minutes with brake on 2. Remove supernatant, resuspend pellet in appropriate media.

Preparing the Patient Cells (from whole blood with Calciparine, or BM Specimen with Calciparine):
Into an appropriate size (depends on sample volume) capped plastic tubes labeled with each patient's name, dispense the appropriate volume of histopague (use equal amounts of histopaque to equal amounts of whole blood, i.e., if a whole blood tube containing 8 ml of blood is received, dispense 4 ml of histopaque and 4 ml of whole blood into each of two 15 ml capped tubes. If 75 ml of BM is received, dispense approximately 18.75 of histopaque and 18.75 of BM into four 50 ml conical tubes. Layer in the whole blood very slowly at a 45° C. angle on the histopaque. Centrifuge at 1600 RPM for 20 minutes in centrifuge at 4° C., brake on 2. Remove and discard the supernatant. Remove the cell interface and place in a separate tube containing 10− RPMI 1× G,G media. Dilute the cells with media quickly because the histopaque is very toxic to the cells if left on them for extended periods of time. Wash cells twice with 10− RPMI 1× G,G media. Centrifuge at 1600 RPM for 5 minutes with the brake on 2. Remove and discard the supernatant. Resuspend the cell pellet in 5 ml RPMI 1× G,G media.

PERFORM CELL COUNT:
In a 12×75 ml glass tube, combine: 0.7 Media; 0.2; Trypan Blue; and 0.1 Cell Suspension. This is a 1:10 Dilution. Mix well. Charge one chamber of the hemocytometer with the cell suspension. Under the light microscope, count the live cells (those which have not absorbed Trypan Blue) in the 4 corner 1 mm$^2$ squares. The concentration of cell lines and patient cells for the IM assay will be as follows (cells per ml):

L-Cells $5 \times 10^5$

Colon $1 \times 10^5$

Prostate $5 \times 10^4$

Breast $5 \times 10^4$

Ovarian $2 \times 10^4$

Patient $1 \times 10^6$

Count the total number of cells (stained and unstained) in the 4 corner 1 mm$^2$ squares.

CALCULATION FOR CELL COUNT:
Use the following cell count formula:

Cells per ml=average # cells× dilution factor×hemocytometer factor.

EXAMPLE CALCULATION:
Patient cells are brought up in 10 ml of media. 0.1 ml of cells are added to 0.2 ml of Trypan Blue and 0.7 ml of media. 4–1 mm$^2$ squares were counted and cell count=80 cells.

20 cells (80 cells 4–1 mm$^2$ squares= average # of cells)×10 (dilution factor)×$10^4$=2×$10^6$ cells/ml.

Calculate % viability using the following formula:

% of viable cells×100=% viability total # of cells

Adjust volume to amount needed for the appropriate cell concentration for the assay:

$(V_1 C_1 = V_2 C_2)$ $V_1 = 10$ ml $V_2 = ?$ $C_1 = 2 \times 10^6$ cells/ml $C_2 = 1 \times 10^6$ cells/ml $$\frac{V_1 C_1}{C_2} = V_2$$

$$\frac{10 \text{ ml} \times 2 \times 10^6 \text{ cells/ml}}{1 \times 10^6 \text{ cells/ml}} = V_2$$

20 ml=$V_2$ 20 ml–10 ml=10 ml

Ten ml of media must be added to have a volume of $1 \times 10^6$ cells/ml.

Label the appropriate number of plates with the following information: 1) Specimen number; 2) Patient name; 3) Name of BRM; 4) Setup date.

Preparing Upper Layer:

Label and arrange 15 ml sterile capped tubes for each control, patient serum, patient whole blood sample, that you need in a test tube rack according to Table 2 (infra.). Be sure to include a cell control, and a control for each BRM to be tested. The cell control should contain everything the others contain except for BRM. A separate set of control tubes must be set up for each cell line assayed (colon, L cell, prostate). Dispense the upper layer stock media into each tube, then add appropriate amounts of BRM, ABIFN, cell line and serum or patient whole blood. See Table 2 as follows:

TABLE 2

FOLLOW THIS TABLE FOR UPPER LAYER VOLUMES (ALL IN ml):

| | UPPER LAYER | BRM | ABIFN | PTWBC OR SERUM | L CELLS | AGAR 1.5% | TOTAL VOLUME |
|---|---|---|---|---|---|---|---|
| CELL CONTROL | 2.1 | — | — | — | 0.3 | 0.6 | 3.0 ml |
| IFN CONTROL | 2.0 | 0.1 | — | — | 0.3 | 0.6 | 3.0 ml |
| IL2 CONTROL | 2.0 | 0.1 | — | — | 0.3 | 0.6 | 3.0 ml |
| ABIFN CONTROL | 2.0 | — | 0.1 | — | 0.3 | 0.6 | 3.0 ml |
| PT. SERUM | 1.9 | — | — | 0.2 | 0.3 | 0.6 | 3.0 ml |
| PT. SERUM/ABIFN | 1.8 | — | 0.1 | 0.2 | 0.3 | 0.6 | 3.0 ml |
| PT. SERUM/IFN | 1.8 | 0.1 | — | 0.2 | 0.3 | 0.6 | 3.0 ml |
| PT. SERUM/IL2 | 1.8 | 0.1 | — | 0.2 | 0.3 | 0.6 | 3.0 ml |
| PT. WBC | 1.9 | — | — | 0.2 | 0.3 | 0.6 | 3.0 ml |
| PT. WBC/SERUM | 1.7 | — | — | 0.2 / 0.2 | 0.3 | 0.6 | 3.0 ml |
| PT. WBC/SERUM/ABIF | 1.6 | — | 0.1 | 0.2 / 0.2 | 0.3 | 0.6 | 3.0 ml |
| PT. WBC/IFN | 1.8 | 0.1 | — | 0.2 | 0.3 | 0.6 | 3.0 ml |
| PT. WBC/IFN/SERUM | 1.6 | 0.1 | — | 0.2 / 0.2 | 0.3 | 0.6 | 3.0 ml |
| PT. WBC/IL-2 | 1.8 | 0.1 | — | 0.2 | 0.3 | 0.6 | 3.0 ml |
| PT. WBC/IL-2/SERUM | 1.6 | 0.1 | — | 0.2 / 0.2 | 0.3 | 0.6 | 3.0 ml |

Add all components except agar to the appropriate tube. For the following, one tube should be finished before moving on to the next. With a 2.0 ml pipet, draw up 0.6 ml of 1.5% agar. Dispense the agar into the tubes one at a time, starting with tube #1. Mix by aspirating and dispensing twice. Draw up 2.2 ml of solution and dispense 1.0 ml into each gridded petri plate (on top of the other layer) taking care not to produce bubbles in the agar. Gently swirl plate to allow for even distribution. Allow agar to solidify, and then add distilled water (approximately 0.5 ml) to humidity plate and place in large labeled petri plate. Repeat steps 5–7 for each plate to be set up. Incubate the cultures at 37° C. in a humid, 5% $CO_2$-enriched atmosphere.

REPORTING RESULTS:

Reading semi-solid culture plates:

Read the plates after 7 days as follows: Scan the plate for colonies and aggregates. If they are present, count all the squares to obtain the number of aggregates and colonies in the plate (aggregates=4–20 cells per cluster) (colony is >20 cells per cluster). If no colonies or aggregates are present, count all individual cells (cell line and patient's WBC's) in 4 squares and take the average. Multiply the average by 15× 13.36 (15=# of square in the center row) (13.36=area of the plate). Plates may be read at 5, 6 or 8 days. Record all data in scientific notation on the report form.

Procedure 4

Human Interferon Assay

Interferons are cytokines that have the ability to inhibit the growth of viruses and to protect infected cells against viral cytopathic effects. The immunoregulatory functions of interferons such as the increase in natural killer (NK) lymphocyte activity, the increase in histocompatibility antigens, the activation of monocyte/macrophages, and B-cell function have also proven to be of clinical importance. The first natural interferon was discovered by Isaac and Linderman in 1975, and recombinant interferon alpha 2 was registered by the FDA in 1986 ushering in a new phase of biotherapy. The goal of this assay is to determine the level of interferon in international units/ml in patient's serum. Potency of the human interferon of serum samples and controls will be determined using WISH cells challenged with Vesicular Stomatitis Virus measuring the cytopathic effect.

SPECIMEN REQUIREMENTS, COLLECTION AND HANDLING

Specimens are labeled with the following information: 1) Patient name; 2) Date drawn; 3) Time drawn; 4) Phlebotomist's initials; 5) Test name.
Serum-Amount required:

Optimum=3.0 ml

Minimum=1.0 ml

The specimen must be aseptically collected in a "tiger" top vacutainer tube, allowed to clot, then centrifuged at room temperature for 10 minutes at 2000 rpm. The serum should be poured over into a sterile plastic tube, capped, appropriately labeled, and stored frozen until the assay is performed.
Plasmapheresis—Amount required:

Optimum=3.0 ml

Minimum=1.0 ml

The specimen must be collected using sterile technique into a 10 ml red top vacutainer tube from the plasma bag obtained during the plasmapheresis procedure. Add 2500 units of calciparine to the 10 ml red top vacutainer tube containing the plasmapheresis sample and mix well. In addition to the information required above, the specimen should be labeled with the bag number from which it was obtained, i.e. #1, #2, etc. The specimen must be poured over into a sterile plastic tube, capped, appropriately labeled, and stored frozen until the assay is performed.
EQUIPMENT:
The following equipment is needed for this procedure:
Sterile laminar flow hood with ultra-violet light
Freezer –70° C.
Refrigerator 2°–8° C.
Autoclave
Analytical balance
Refrigerated centrifuge
$CO_2$ incubator
Spectrophotometer (Bio-Rad 96-well plate reader with 540 nm filter)
96-well microtiter plates—sterile flat bottom with covers Falcon 3872
Pipet aid
Micropipettes
Costar octapettes—50 ul, 100 ul, & 200 ul
Wheaton multi-channel pipet—50–200 ul range
MLA-40 ul
Sterile disposable:
Pipettes (1 ml, 5 ml, 10 ml, and 25 ml)
Pipet tips Wheaton 851247
Plastic troughs
Gauze
Cryovials
50 ml conical tubes with caps
Test tubes
Culture flasks (75 cm and 150 cm)
Kimtex wipers
Biohazardous waste can and bags
Stainless steel pan with cover
MATERIALS:
The following materials are needed for this procedure:
Basal Medium Eagle 1× (BME), 500 ml Gibco Cat. No. 320-1010AJ
Fetal Bovine Serum, 100 ml Hyclone Cat. No. A-1111-D
L-Glutamine, Cat. No. 320-5030AG
Hepes Buffer Solution (1M), 100 ml Gibco Cat. No. 380-5630AG
Penicillin/Streptomycin
WISH cells (Human Amnion) ATCC 25-CCL
Vesicular Stomatitis Virus ATCC
Human Interferon (alpha) Reference NIAID Cat. No. Ga23-902-530
Gamma Interferon control
Neutral red dye Sigma No. N-2880
Phosphate buffered saline (PBS)
PBS without Ca++ and Mg++, Ph 7.4 Gibco Cat. No. 310-4190AJ
PBS with Ca++ and Mg++, Ph 6.8 Gibco Cat. No. 310-4040AJ
Glacial acetic acid Sigma Cat. No. A-6283
Distilled water
Ethyl Alcohol Aldrich Cat. No. 18,738–0
Patient sera
One-Stroke Environ Calgon Vestal No. 539708
Trypsin-EDTA 1×, 100 ml Gibco Cat. No. 610–5200AG
Trypan Blue Gibco 6305250AG
REAGENT PREPARATION:
All media must be filtered for sterility, labeled with name, preparation and expiration dates, storage information, and technician's initials. Prepared media is stable for three months at 2°–8° C.
BME with 15% FBS:
Add 75 ml of FBS, 5.0 ml Pen/Strep 10 ml glutamine, and 5 ml hepes to a 500 ml bottle of BME. (For feeding WISH cells.)
BME with 10% FBS:
Add 50 ml of fetal bovine serum, 2.5 ml Pen/Strep, 10 ml glutamine, and 5 ml hepes to a 500 ml bottle of BME.
BME with 2% FBS:
Add 10 ml of FBS, 2.5 ml Pen/Strep, 10 ml glutamine, and 5 ml hepes to a 500 ml bottle of BME.
Vesicular Stomatitis Virus (VSV):
Prepare two 150 $cm^2$ culture flasks of WISH cells. Discard the media when the cells become confluent. Wash once with fresh BME with 2% FBS. Dilute a VSV stock preparation 1000 times with BME with 2% FBS. Inoculate 8–10 ml per flask of the 1:1000 VSV into each WISH cell flask such that it covers the entire cell layer. Incubate the flasks for 1 hour at 37° C. in a 5% CO2 incubator. Add 15 ml of the BME with 2% FBS to each flask and incubate at 37° C. in a 5% CO2 incubator for 1–3 days or until cell layers show nearly complete viral cytopathic effect (CPE). Harvest the culture fluid and clarify by centrifugation at 3000 RPM for 20 minutes at 4° C. Aliquot the virus containing supernatant into 10 ml tubes and store at –70° C. This virus stock usually contains $1 \times 10^9$ plaque-forming units/ml when its infectivity is quantitated in WISH cells. Dilute one 10 ml stock VSV tube 1:10 with BME with 2% FBS to yield a working VSV of 1×10$^8$ plaque forming units/ml. Aliquot 1 ml of working VSV into cryovials and store at −70° C. Dilutions of 1:100, 1:200, and 1:300 of working VSV should be made and inoculated onto confluent WISH cells in a 96-well plate to determine the dilution that yields nearly 100% CPE in 24–48 hours.

Human Alpha Interferon (National Institute of Health: catalog #Ga23-902-530):

Reconstitute with 1.0 ml of sterile distilled water being careful to avoid any loss of material in the neck of the ampule. Dilute to a concentration of 105 IU/ml of interferon with BME with 2% FBS (no Pen/Strep and no hepes). Aliquot 200 ul into cryovials and store in −70° C. freezer. The aliquots are stable for two years at this temperature.

Neutral Red Dye:

Prepare 0.1% stock solution of Neutral Red Dye by adding 500 mg of red dye powder to 500 ml of distilled water. Mix with magnetic stir bar at room temperature for 1 hour. Autoclave for 10 minutes at 15 psi. Cool. Label and store stock Neutral Red Dye in a brown bottle and refrigerate. Staining Solution—prepare a 15% staining solution by adding 85 ml PBS with Ca$^+$+ and MG$^+$+ (Ph 6.85) to 15 ml stock Neutral Red Dye.

Eluting Solution:

To 1 ml glacial acetic acid add 49 ml distilled water and 50 ml 100% ethanol. Label and store in glass capped bottle at room temperature.

Gamma Interferon Control:

Obtain Actimmune (3.0×10$^6$ units/ml). Dilute 0.05 ml (50 ul) of Actimmune with 49.95 ml of BME with 2% FBS and mix well to obtain a concentration of 3000 units/ml. Aliquot 10 ml into each of 5 sterile capped tubes and label with "stock IFN gamma," 3000 units/ml, preparation and expiration dates. (Stable for 2 years at −70° C.). Dilute 1 ml of stock IFN gamma with 9.0 ml of BME with 2% BME for a working concentration of 300 units/ml. Aliquot 200 ul of this concentration into cryovials, label, and store at −40° C. (Stable for 2 years.). Run in parallel with current control to obtain range prior to putting into use.

PROCEDURE:

Day One:

Generate a worksheet from the interferon data base for 24 samples. Number the worksheet with #1 as the reference, patient samples #2–#25, the gamma control #26, and the alpha control #27. Retrieve the patient samples, interferon reference and controls from the freezer. Verify samples with the worksheet. Label nine sterile 96-well microtiter plates with sample numbers (run in duplicate), plate number and date. Two 150 cm$^2$ flasks of confluent WISH cells are harvested and washed by the liquid culture technician. The tube of cells is labeled with the name of the cells, the passage number, date, and technician's initials. Note: The passage of WISH cells should be less than P250. Before this passage is reached, cells of younger passage should be retrieved from liquid nitrogen and started in liquid culture.

Perform the cell count in the following manner: in a 12×75 ml tube, combine 0.5 ml of WISH cells and 0.5 ml of 0.4% Trypan Blue (1:2 dilution). Mix well and charge the hemacytometer chamber. Under the light microscope, count the viable WISH cells in the four corner 1 mm$^2$ squares and divide by 4 to obtain the average for 1 square. Count the total number of cells in the four corner 1 mm$^2$ squares and divide by 4 to obtain the average for 1 square. Determine the % viability by dividing the viable cell count by the total cell count and multiplying by 100. Record the % viability on the cell count worksheet.

Determine the number of cells/ml by using the following equation:

Avg. # of viable cells/square× dilution factor×hemacytometer factor=cells/ml

Dilute the WISH cells to 3.5×10$^5$ cells/ml according to the following formula:

$$V_1C_1=V_2C_2$$

For example:

Volume$_1$=40 ml Concentration$_1$=2.0×10$^6$
Volume$_2$=? Concentration$_2$=3.5×10$^5$ $$\frac{V_1C_1}{C_2} = V_2$$

$$\frac{40 \text{ ml} \times 2.0 \times 10^6 \text{ cells/ml}}{3.5 \times 10^5 \text{ cells/ml}} = V_2$$

V$_2$=229 ml

Add 189 ml of BME with 10% FBS to the original volume of 40 ml to obtain 3.5×10$^5$ cells/ml. Set aside diluted WISH cells until ready to be added to the microtiter plates. Using sterile techniques, add 100 ul of 10% BME to each well (including blanks) of the 96-well microtiter plates. To the wells in column #1, B–G, add an additional 60 ul of 10% BME. To well positions B1 and C1 of plate #1 (each sample will be run in duplicate) add 40 ul of the reference. To well positions D1 and E1 add 40 ul of patient serum. To each successive pair of wells, add 40 ul of the appropriate patient serum. In addition to the patient samples, set up a gamma interferon control and an alpha interferon control (reference) on the last plate of the assay. Make serial dilutions with the 100 ul octapet from column 1 to column 10 and rows B–G by mixing up and down several times, then carrying 100 ul to the next column through the 10th column. Discard the remaining 100 ul from the 10th column. Add 100 ul of the 3.5×10$^5$ cells/ml WISH cell suspension to all wells except blank wells in rows A and H. Designate column 11 as cell control and column 12 as viral control on each plate. Incubate plates 18–24 hours at 37° C. at 5% CO$_2$. Lay out the stainless steel pan containing OneStroke Environ, diapers and gauze squares in hood with white light overnight.

Day Two:

Check plates under the inverted microscope for confluency. Check for toxicity of patient sera (black edges). Using sterile techniques, dump the media from the plates into the stainless steel pan containing OneStroke Environ, blot on gauze. Wash the cells by adding 100 ul of BME with 2% FBS to all the wells except the blank wells, dump, and blot. Add 50 ul of 2% BME to column 11. Add 100 ul of 2% BME to all wells (including blanks). Add 50 ul VSV (in a concentration that yields 90% CPE in the viral control in 24–48 hours) to all the sample wells in columns 1–10 and column 12. Incubate 24–48 hours at 37° C. with 5% CO$_2$.

Day Three:

Check plates under the microscope for 90– 100% CPE in the viral control. Look for 50% CPE in the reference and samples. The 50% CPE should fall between columns 4 and 6 for the reference. Incubate plates until this is achieved. Place the stainless steel pan containing One-Stroke Environ along with Kimtex wipers sufficient for blotting the plates under the hood. Dump plates and blot. Add 100 ul of 15% neutral red dye to all the sample wells. Incubate at 37° C. with 5% CO$_2$ for 45 minutes. Dump plates and blot. Rinse with 200 ul PBS at pH 6.85. Dump and blot. Plates may be left to dry inverted on Kimtex wipers on a tray for several days before eluting. Elute by adding 100 ul of the eluting solution to each sample well.

Read on the microplate reader with a 540 nm filter. Select Microman from the menu to access the Microplate Manager program. Under Analysis, select Multiple Readings. Select:

Single Wavelength
540 nm
Mixing duration—5 seconds
Reading per plate—1
Number of plates—9
Filename—date (i.e., 0722)

Remove cover of microtiter plate #1 and place in the reader. Select Start. After all the plates have been read, print the raw data reports as follows: Under file, select Open and Lotus Results. Arrow down to filename, or type in the file name and plate number. Select Open. If message appears "Save current results . . . ," say NO. When Raw Data Report appears on the screen, under File, select Print. Select Raw Data Report and OK. Under file select Close. Repeat for each plate to be printed.

RESULTS:

A. Average the optical density (O.D.) values for the cell controls (column 11) and viral controls (column 12).

B. Average the O.D. values for the duplicates of the patients and reference samples—i.e. average B & C for each column 1–10, average D & E for each column 1–10, etc.

C. To determine the O.D. at 50%:

$$\frac{X \text{ Virus Controls} + X \text{ Virus Controls}}{2} = OD$$

D. To enter the O.D. values and their corresponding IFN dilutions:

1. Enter the 1st average O.D., press X− Y
2. Enter corresponding 1st IFN dilution, press LOG, then E+
3. Enter the 2nd average O.D., press X− Y
4. Enter corresponding 2nd IFN dilution, press LOG, then E+
5. Enter the 3rd average O.D., press X− Y
6. Enter corresponding 3rd IFN dilution, press LOG, then E+

E. To determine the correlation coefficient (r):

1. Press 2nd, then CORR (÷)
2. The correlation coefficient (r) should be −1.0±0.1.
3. Enter O.D. 50%, press 2nd, then y' (x)

F. To convert the titer (log 10) to units/ml, press INV, then LOG

G. To clear data, press 2nd, then STO, then CE/C

H. To convert IFN units/ml to International Reference Units/ml:

1. IFN units/ml of Reference=Factor Int'l Ref. Units/ml of Reference
2. Sample IFN units/ml=Sample titer (IRU/ml) Factor Procedure 5

Human Tumor Colony-Forming Chemosensitivity Assay (Pharmacosensitivity)

The Human Tumor Colony Assay (HTCA: clonogenic or tumor stem cell assay) is an in vitro culture system employing semi-solid medium support originally described by Salmon and Hamburger, et al. Using HTCA, the growth and chemosensitivity of clonogenic tumor cells present in fresh biopsy specimens of human tumors can be investigated. Since this technique was first described, there has been a marked increase in the direct study of human tumors in vitro. Excellent evidence has been obtained which establishes that colonies grown in HTCA are comprised of tumor cells and that clonogenic cells within tumor colonies have the property of self-renewal (the defining property of a tumor stem cell). Chemosensitivity testing with specific agents in HTCA has documented striking degrees of heterogeneity in drug sensitivity from patient to patient, even for tumors of the same histopathology. Clinical correlations have been made between in vitro chemosensitivity and the response of patients with metastatic cancer to chemotherapy. In a series of trials, HTCA has had a 71% true-positive rate and a 91~true-positive rate for predicting the drug sensitivity and resistance, respectively, of cancer patients to specific chemotherapeutic agents. The assay thus appears to be a prognostic factor which identifies chemosensitive patients and which may allow some individualization of chemotherapy.

Tumor specimens, either from solid tumor masses, malignant ascites, or bone marrow are mechanically disaggregated into a suspension which is as close to a "single-cell suspension~as possible. These cells along with chemotherapeutic agents, biological response modifiers, and hormones are suspended in an agar-containing culture medium and then layered or "plated" onto a semi-solid underlayer. The underlayer prevents normal human fibroblasts, a major tumor stromal component, from adhering to the culture dish bottom and forming colonies which might be confused with colonies of tumor-cell origin. After 7 days, 14 days, and 21 days of incubation in a humid, CO2-enriched atmosphere at 37° C., colonies (greater than 20 cells) and aggregates (4–20 cells) are counted. A negative control and a positive control are set up for each tumor. From this data the effect of each specific drug on the tumor can be determined.

SPECIMEN REQUIREMENTS, COLLECTION AND HANDLING:

This assay may be performed on the following specimen types:

Solid tumors obtained during surgery or biopsy
Bone marrow aspirates and biopsies
Ascites
Pleural fluids
Thoracentesis fluids The sample should be sufficient to yield an optimum of 20 ml of $1.0 \times 10^6$ viable cells/ml. A minimum of 12 ml of $1.0 \times 10^6$ viable cells/ml is acceptable. All specimens should be labeled with patient name, collection date, tumor type, and initials of technician.

MATERIALS:

The following materials are needed for this procedure:

Laminar Flow Hood
Bacto-Agar
Analytical Balance
Weighing Paper
Weighing Tools
Sterile Capped Bottles (100 ml, 250 ml, 500 ml; and 1,000
Distilled Water
Microwave Oven
Autoclave
RPMI 1640 Media (1× and 2×)

HCL (1N)
Sodium Bicarbonate
Penicillin/Streptomycin
Disposable Pipettes (sterile) (1 ml; 2 ml; 5 ml; 10 ml, 25 ml)
Select-A-Pette Pipetter (1 ml)
Select-A-Pette Tips (sterile)
Eppendorf Pipettes
Eppendorf Combitips (sterile) (2.5 ml; 5.0 ml; 12.5 ml)
Glutamine
Trace Elements
2-Mercaptoethanol With Dulbecco's PBS
ITS Solution
Fetal Bovine Serum
Test Tubes (12×75 Glass-disposable; 15 ml Capped-sterile and disposable)
Petri Dishes (sterile) (Routine-100×15 mm; Gridded Plates-35×10 mm)
Sterile Capped 50 ml Conical Tubes (Falcon)
Homogenizer
Trypan Blue Stain (0.4~)
Hemocytometer With Cover Slips
Microscopes (Inverted; Light)
Hand Tally Counter
Ph Paper (narrow spectrum)
Graduated Cylinders (50 ml and 100 ml)
Histopaque-1077
Water Bath
Pipet Suction Aide
Refrigerated Centrifuge
Liquid Culture Flasks (25 cm$^2$)
$CO_2$ Incubator
Chemotherapeutic Drugs
Biological Response Modifiers
Hormones
Vortex Mixer
Refrigerator (2°–10° C.)
Scalpel (disposable and sterile)
Sharps Container Pasteur Pipettes 5¾" (disposable)
Dropper Bulbs
–70° C. Freezer
Precise Surface Disinfectant
70% Alcohol In Squeeze Bottle
Contrad Glassware Disinfectant/Cleanser
Thermometer (–20° C.–120° C.)
Beaker (500 ml)
Betadine Disinfecting Solution
Syringes (disposable and sterile) (1 cc; 10 cc)
Needles (various gauges)

MEDIA AND REAGENT PREPARATION:
Agar:
Lower layer=2.5% working solution: Measure out 2.5 gm of Bacto-Agar and place in a 100 ml capped bottle. Add 100 ml distilled water. Swirl gently to mix.
Upper layer=1.5% working solution: Measure out 1.50 gm of Bacto-Agar and place in a 100 ml capped bottle. Add 100 ml distilled water. Swirl gently to mix.
Place both bottles in the microwave with caps loosened. Microwave for 60 seconds at full power, mixing every 20 seconds. Avoid boiling. The agar will appear clear when ready. If the solutions boil over, do not use, remake the agar. Place a piece of autoclave tape on each of the loosely capped bottles and autoclave the solutions for 20 minutes at 22 psi. Place both bottles in the water bath under the hood. THIS BATH MUST BE KEPT AT 45°– 50° C. AT ALL TIMES. The agar should cool down to 50° C. before use. Swirl agar to mix well before using. After preparation of each media, label the final product according to procedures previously described.

MEDIA:
10% RPMI 1640 (1×):

| AMOUNT | COMPONENT |
| --- | --- |
| 500.0 ml | RPMI 1640 (1X) with L-Glutamine |
| 50.0 ml | Fetal Bovine Serum, Qualified, Heat Inactivated |
| 5.0 ml | L-Glutamine (100X) 200 mM |
| 1.5 ml | Penicillin/Streptomycin |
| 2.0 ml | Trace Element Mix (100X) Lyophilized |
| 0.5 ml | 2-Mercaptoethanol |
| 5.0 ml | Insulin-Transferrin-Sodium Selenite Media Supplement, Lophilized, Gamma-Irradiated |

Combine all components under a sterile laminar flow hood. Sterilize by filtration using a 0.22 micron membrane filter with a 60 micron prefilter. Label and store the prepared media at 2°–10° C.

10% RMPI 1640 (2×) G,G Fortified:

| AMOUNT | COMPONENT |
| --- | --- |
| 500.0 ml | RPMI 1640 (2X) Powdered Cell Culture Medium With L-Glutamine (Reconstitute one powder pack with a total of 500.0 ml of sterile DISTILLED WATER) |
| 50.0 ml | Fetal Bovine Serum, Qualified, Heat Inactivated |
| 5.0 ml | L-Glutamine (100X) 200 mM |
| 2.5 ml | Penicillin/Streptomycin |
| 2.0 ml | Trace Element Mix (100X) Lyophilized |
| 0.5 ml | 2-Mercaptoethanol |
| 5.0 ml | Insulin-Transferrin-Sodium Selenite Media Supplement; Lophilized; Gamma-Irradiated |

Under a sterile laminar flow hood, measure out 450 ml of sterile distilled water and place in a sterile 500 ml reagent bottle. Add the powdered medium to the water with gentle stirring. Rinse out the inside of the package to remove all traces of powder. Add 1.0 G OF $NaHCO_3$ per. 500 ml of medium. Dilute with sterile $DH_2O$ to 500 ml volume. Adjust the pH of the preparation to 0.2– 0.3 below the desired final working pH of 7.2 (pH units will usually rise 0.1–0.3 upon filtration); use of 1N NaOH or 1N HCl is recommended. After the Ph has been adjusted, keep the container closed until the medium is filtered. Sterilize immediately by membrane filtration using a 0.22 micron membrane filter with a 60 micron prefilter (positive pressure is recommended). Label and store the prepared media at 2°–10° C.

Lower Layer Stock Media:
125 ml Fetal Bovine Serum
125 ml 2×G,G Fortified Solution
250 ml 1×G,G Fortified Solution
Mix, label, and store at 2°–10° C.

Upper Layer Stock Media:

150 mlFetal Bovine Serum 150 ml2×G,G Fortified Solution 150 ml1×G,G Fortified Solution Mix, label, and store at 2°–10° C.

Preparation of Drugs:

Working aliquots of each drug, hormone, and biological response modifier are prepared every two weeks according to the aliquot procedure. The working aliquots are stored at 4° C. and are ready for use.

PROCEDURE:

Prepare the Lower Layer Tubes:

Pipet 8 ml of lower layer stock media into 15 ml sterile capped tubes. (NOTE: Determine the number of plates needed by multiplying the number of drugs on the testing panel ×2. One lower layer tube yields approximately 8 lower layer plates.) Keep capped at room temperature until needed to prepare lower layer plates or store capped overnight at 28° C. for use the following day. Be sure to warm to room temperature before use.

Plate the lower layer plates as follows (WORK QUICKLY TO PREVENT PREMATURE SOLIDIFICATION OF THE AGAR): With a sterile 10 ml pipet, draw up 2.0 ml of the 2.5% agar mixture. Dispense the 2.0 ml of agar into one of the 15.0 ml plastic tubes containing 8 ml of lower layer media and mix twice by drawing up and dispensing into the tube. Draw up 9.0 ml of the mixture and dispense 1.0 ml into each of eight sterile 35 mm gridded plates. Swirl to cover the bottom of the plate. Take care to prevent bubbles. Allow plates to sit undisturbed on a flat surface until the agar has solidified. Discard any plates with uneven agar distribution. Store plates at room temperature for same day use or store overnight ln a 37° C. CO2 incubator for use the following day.

Prepare the Cell Suspension:

Solid tumor: In a sterile petri dish, using sterile scalpel and forceps, cut the tumor specimen into pea-size portions. Save the original transport media for centrifugation. Place the specimen in a glass conical tube that has a matched loose-fitting homogenizer. Add 5.0 ml of transport media. Gently homogenize the tumor pieces a small portion at a time and transfer the cell suspension to a sterile 50 ml conical tube. When all of the tumor has been homogenized, mix well and then allow cell suspension to settle, undisturbed, for one minute (this will allow clumps of tissue to settle out). Pipet the supernatant into a sterile tube, dilute with RPMI 1× with 10% FBS and centrifuge at 1600 RPM for 5 minutes. Remove the supernatant, resuspend the cells in RPMI 1× with 10% FBS, and perform cell count and viability.

Liquid tumor (ascites, bone marrow, etc.): Using a sterile pipet, dispense 20–25 ml of histopaque into the appropriate number of capped sterile 50 ml conical tubes. Using another sterile pipet, gently layer the ascites, bone marrow or cell suspension at a 45° C. angle onto the histopaque using a 1:1 ratio of histopaque to specimen. Centrifuge at 1600 RPM for 20 minutes in the refrigerated centrifuge at 4° C. (brake on 2). Remove and discard the supernatant. Remove the cell interface and place in RPMI (1×) GG fortified in a pre-labeled tube. DILUTE THE CELLS WITH THE MEDIA QUICKLY BECAUSE THE HISTOPAQUE IS VERY TOXIC TO THE CELLS IF LEFT ON THEM FOR EXTENDED PERIODS OF TIME. Wash cells twice with RPMI 1640 (1×) media and centrifuge at 1600 RPM for 5 minutes with a brake of 2. Remove and discard the supernatant. Resuspend the cell pellet in 5 ml of RPMI 1× medium.

Perform Cell Count:

In a 12×75 ml glass tube, combine:

0.1 ml of well-mixed cell suspension 0.2 ml of 0.4% Trypan Blue stain 0.7 ml of media This is a 1:10 Dilution.

Mix well and charge one chamber of the hemocytometer with the cell suspension. Under the light microscope, count the viable tumor cells (those which have not absorbed the Trypan Blue) in the four corner 1 mm$^2$ squares. Count the total number of tumor cells (stained and unstained) in the four corner 1 mm$^2$ squares.

Calculation for Cell Concentration:

Perform the viable cell count using the following equation:

Average # of viable cells per square× dilution factor×hemacytometer factor

Sample calculation:

20 Cells (average # of viable cells per square)×10$^4$×10 (dilution factor)=2× 10$^6$ cells/ml.

Determine the % viability using the following formula:

$$\frac{\text{viable cell count}}{\text{total cell count}} \times 100 = \% \text{ viability}$$

Adjust volume to amount needed for the appropriate cell concentration for the assay (this assay requires 1×10$^6$ cells/ml) using the following formula:

$$(V_1 C_1 = V_2 C_2)$$

For example:

$V_1$=10 ml $V_2$=?

$C_1$=2×10$^6$ cells/ml $C_2$=1×10$^6$ cells/ml $$\frac{V_1 C_1}{C_2} = V_2$$

$$\frac{10 \text{ ml} \times 2 \times 10^6 \text{ cells/ml}}{1 \times 10^6 \text{ cells/ml}} = V_2$$

20ml=$V_2$ 20 ml–10 ml=10 ml

Ten ml of media are needed to have a volume of 1×10$^6$ cells/ml.

Prepare Upper Layer Tubes:

Pull and arrange the prepared drugs that are to be tested against the tumor cells. Label the appropriate number of 15 ml capped tubes with the names of the drugs. Arrange the tubes in a test tube rack. Use the Table 3 as follows for upper layer volumes (all in ml):

TABLE 1

|  | UPPER LAYER MEDIA | CELLS | DRUGS | AGAR 1.5% |
| --- | --- | --- | --- | --- |
| CONTROL | 2.1 | 0.3 | — | 0.6 |
| ABRIN | 1.8 | 0.3 | 0.3 | 0.6 |
| DRUG #1 | 1.8 | 0.3 | 0.3 | 0.6 |
| DRUG #2 | 1.8 | 0.3 | 0.3 | 0.6 |
| DRUG #3 | 1.8 | 0.3 | 0.3 | 0.6 |

Add all components except agar to the appropriate tubes. For the following steps, one tube should be finished before moving on to the next. With a 2.0 ml pipet, draw up 0.6 ml of 1.5% agar. Dispense the agar into the tube, one at a time, starting with tube #1. Mix by aspirating and dispensing twice. Draw up 2.2 ml of the solution and dispense 1.0 ml into each of two gridded plates (on top of the other layer) taking care not to produce bubbles in the agar. Gently swirl plate to allow even distribution. Allow agar to solidify undisturbed, and then add approximately 0.5 ml of distilled water to a third "half plate" in the large petri dish labeled with the corresponding drug. Repeat steps 5–7 for each drug to be tested. Incubate the cultures at 37° C. in a humid, 5% $CO_2$ enriched atmosphere.

Liquid Culture:

With the remaining cell suspension liquid cultures as follows: Label two 25 cm² liquid culture flasks. Add RPMI 1640 1× Fortified plus FBS and cell suspension to the flasks as follows:

|  | MEDIA | CELLS |
|---|---|---|
| 25 cm² | 4.0 ml | 0.5–1.0 ml |

Incubate the cultures at 37° C. in a humid, 5% $CO_2$ enriched atmosphere. Leave the caps loose for $CO_2$ exchange.

DNA Analysis:

If requested by the physician, save at least 1 ml for DNA. (NOTE: The cells do not need to be alive for DNA testing.) Label the tube with the patient name, date, specimen type, and tracking number and place in the DNA beaker in the refrigerator.

Liquid Nitrogen:

Prepare a minimum of 2 cryovials for long-term storage in liquid nitrogen according to the freezing protocol.

Immunomodulation:

If requested by the physician, save at least 2.0 ml for the assay and store refrigerated until the IM assay is performed.

Reporting Results:

Within 24 hours after setting up the pharmacosensitivity, read the cell control and abrin plates under the inverted scope. Scan the plates in entirety. Count any clumps of cells and record as a background count on the worksheet. Always scan the entire plate for colonies and aggregates using a hand tally counter to record the number of each. If no colonies or aggregates are present, count the number of cells in four squares. Divide by 4 to obtain the average number of cells in one square, multiply by 15, then by 13.36 to obtain the number of cells in the entire 35 mm plate. Use scientific notation to report the colonies, aggregates and/or cells for any number greater than 3 digits. Representative colonies, aggregates, and/or cells must be photomicrographed and logged in the log book prior to discarding plates. Verify that controls fall within expected range. If not, document in the comment section and notify the Supervisor immediately. Do not discard the assay; it may be accepted at the discretion of the Medical Director.

Experiment 1

Activity of *N. sativa* on bone marrow cells

Preparation of *N. sativa:*

1. Dried seeds are finely ground, and 5 grams (5 g) of the powder is extracted with 95% ethanol 3 times, by soxhlet extraction. A Wheaton soxhlet extraction apparatus consists of 3 parts: the bottom part is the flask in which the 95% ethanol is heated; the middle portion is the extractor; and the top the Allihn condenser, in which there is an inlet and outlet for running cold water through the condenser. Dried *N. sativa* seed powder is packed in filter paper and placed in the extractor.

2. The pooled extracts are evaporated under reduced pressure to a known volume of 10 ml and loaded onto a silica gel (Keiselgel 60: Fluka) column and eluted with 95% methanol/water (9:1). In the column, silica gel suspended in methanol/water is layered on sand. *N. sativa* extract is added on top of the silica gel, followed by the eluting solvent.

3. The active fraction (as indicated by brown color) is collected and separated by preparing thin layer chromatography (TLC). On commercially available chromatography plates, a band of *N. sativa* active compound is spotted and run in a TLC jar using chloroform as the solvent system.

4. The active spot at the solvent front is removed, eluted with methanol (overnight), and evaporated under reduced pressure to render the product alcohol free.

5. The extract is then available as a soluble solution and is then stored at 2° C.

The approximate content of the active compound in the seed in 2.2% (w/w).

Calculation of active compound in *N. sativa* extract proceeded as follows: the active compound present in seed extract is 2.2% w/w. One gram of seeds was added to 10 ml assay media. Therefore, active compound added was 22 mg/ml media. Finally 40 µl from this was taken for assay. Hence, the active compound actually added was 88 µg. This was further diluted 1:10, 1:100 and 1:1000 to have a working concentration of 8.8 µg, 880 ng and 88 ng respectively.

Colony Forming Unit Assay

Specimen: Bone marrow sufficient to yield an optimum of 5.0 ml mononuclear cells at a concentration of $1.0 \times 10^6$ cells/ml was collected.

Assay: The assay was performed according to a modified process Metcalf (1984, 1985), which is incorporated herein by reference. The process is described in detail above in Procedure 2. To each 25 $cm^2$ flask, $1 \times 10^6$ bone marrow cells are added, and incubated at 37° C. with 5% $CO_2$ and 100 µl of *N. sativa* plant extract.

Immunofluorescence Staining of Cells: The peripheral blood cells were collected aseptically. For every panel of analysis 3.0 ml whole blood was needed. The assay was conducted according to processes disclosed in and partially modified from Karen (1989) and Merkel et al. (1987), which are incorporated herein by reference. The process is described in detail above in Procedure 1.

The *N. sativa* plant extract was incubated with peripheral blood cells from cancer patients over an 18 hour period at 37° C. in a 5% $CO_2$ incubator. Gates for the antibodies CD3, CD19, HLADR, LAK CD3+/CD56+, NK CD3− /CD56+, CD38, CD37, and CD33 surface markers were set on a Becton Dickinson FacScan serial No. 81326. These antibodies are designed to assist in the characteristics of the types of cells. The cluster designation (CD) is used to group two or more mABs that have statistically similar expression on normal and neoplastic cells and cell lines, as well as similar recognition of the same antigen or binding site (epitope). While mABs in a CD group usually define different epitopes on the same antigen, some CD groups, primarily non-lymphoid clusters, contain mABs that do not bind to the same antigen.

The results obtained from Experiment 1 were compared with that of bone marrow growth factors and biological response modifiers namely GM-CSF, G-CSF, erythropoietin, interferon, IL-2 and STS.

At days 7, 14 and 21, each flask was scanned under a Reichart Jung Biostar inverted microscope. A colony is defined as 40 or more cells adhering to the bottom of the flask.

The colony forming cell unit (CFU) assay on $1\times10^6$ bone marrow cells obtained from 2 cancer patients was performed with and without incubation with 100 µl of *N. sativa* plant extract.

Results: The colony forming cell unit assay on $1\times10^6$ bone marrow cells post 15 days incubation with 100 µl of plant extract showed a 600% elevation. This elevation was 125% after 21 days of incubation. Among the different growth factors/biological response modifiers, IL-2 and GM-CSF gave the maximum elevation of 120 and 115% after incubation with bone marrow cells for 15 days. There was not much detection of CFU elevation post 21-day incubation with growth factor/biological response modifiers. Interferon showed marginal elevation after a 15-day incubation, but negligible detectable response after 21 days.

*N. sativa* plant extract helps restore the immune competent cells in immunosuppressed cancer patients. The colony forming cell unit assay indicates increase in CFU count when bone marrow cells from cancer patients were incubated with *N. sativa* plant extract as well as with different growth factors indicating that *N. sativa* plant extracts mimic the potential application of these several growth factors. Even though the plant extract was used without dissolving, it had no toxic effects against human bone marrow cells. Hence, *N. sativa* plant extract helps restore the immune competent cells in immunosupressed cancer patients and over-stimulates bone marrow in normal individuals.

Experiment 2

Correlation Between Elevation in Immune Competent Cells/Hematopoiesis and *N. sativa* Extract Immunomodulatory Testing Immunomodulatory testing evaluates the activity of patients' sera and white blood cells in relation to interferon, interleukin and lymphokine demonstrating the presence of interferon inhibitor factor and lymphokine inhibitor factor in the experimental procedure. A detailed description of immunomodulatory testing is found above in Procedure 3.

To test for possible correlation between elevation in immune competent cells/hematopoiesis and *N. sativa* extract, the various surface markers of immune competent cells were analyzed by automated flow cytometry as described above in Procedure 3.

The results indicate an elevation in CD19, HLADR, NK CD3–/CD56+ and CD38 population. There was not much alteration in CD3, CD37 and CD33 surface marker index. A proliferation of connective tissue 'L' cells was observed upon incubation with cancer patient serum and *N. sativa* extract at 37° centigrade in 5% $CO_2$ incubator for 7 days.

Cell Line: The mouse connective tissue L929 cells were obtained from the ATCC and grown in MEM medium (GIBCO) with 20% fetal equine serum (BioWhittaker) as described above.

Assay: The assay was conducted according to the process described in Medenica, et al. (1990), which is incorporated herein by reference. Proliferation of $5\times10^5$ 'L' cells/ml was checked on a double layer agar procedure in which lower 1.5% agar layer media contained 125 ml FBS, 125 ml 2× G.G. fortified solution and 250 ml 1× G.G. fortified solution. The upper layer stock media contained 150 ml FBS, 150 ml 2× G.G. fortified solution and 150 ml 1× G.G. fortified solution. To 2.0 ml of upper layer, 0.1 ml of *N. sativa* extract, 0.3 ml of 'L' cells and 0.6 ml of 1.5% agar was added to make a total volume 3.0 ml. Growth of 'L' cells were analyzed under an inverted microscope type Reichert Jung biostar post incubation at 37° centigrade and 5% $CO_2$ after 7 days.

The results are illustrated in Table 4 as follows:

TABLE 4

| INCUBATION MIXTURE | CELL NUMBER | % ELEVATION |
|---|---|---|
| 'L' CELLS & MEDIA | $2.0 \times 10^4$ | 0 |
| 'L' CELLS & IFN & MEDIA | $2.7 \times 10^4$ | 35 |
| 'L' CELLS & IL-2 & MEDIA | $2.3 \times 10^4$ | 15 |
| 'L' CELLS & SERUM & PLANT EXTRACT | $4.7 \times 10^4$ | 135 |
| 'L' CELLS & WBC & PLANT EXTRACT | $7.4 \times 10^4$ | 270 |

Connective tissue 'L' cells at a concentration of $5\times10^5$ were incubated with IFN, IL-2 or plant extract at 37° C. in a humid 5% $CO_2$ incubator for 7 days. The SD of the data was <10%.

Results: Peripheral blood cells from cancer patients upon incubation with *N. sativa* extract over an 18-hour period at 37° C. in 5% $CO_2$ incubator showed elevation in CD19, HLADR, NK CD3–/CD56+ and CD38 populations as shown in FIG. 1. CD19 surface marker index showed an elevation of 90% as compared to control, while HLADR, NKCD3–/CD56+ and CD38 population showed elevations of 44, 38 and 5% respectively. There was not much alteration in the CD3 population.

*N. sativa* extract, rather than the increase in immune competent cell number, helped free tumor antigen binding sites on B cells, thereby elevating the CD19 and associated cell population. Data from flow cytometric analysis indicates elevation in CD19, HLADR, NK CD3–/CD56+ and CD38 population. There was not much alteration in CD3, CD37 and CD33 surface marker index. This data clearly indicates proliferation in immune competent cells, mainly the humoral response against tumor antigens. Thus, the extract, rather than the increase in immune competent cell number, helps free tumor antigen binding sites on B cells, thereby elevating the CD19 and associated cell population.

Connective tissue 'L' cells at a concentration of $5\times10^5$ upon incubation with *N. sativa* plant extract and patient serum/white blood cells showed elevation in cell number. 'L' cells when incubated with media alone was $2.0\times10^4$, which increased to $4.7\times10^4$ and to $7.4\times10^4$ upon incubation with cancer patient serum and plant extract and cancer patient white blood cells and plant extract, respectively. This indicated an elevation of 135 and 270% respectively as shown in Table 4 (supra.) On the other hand, interferon and interleukin-2 gave marginal elevations of 35 and 15% only upon incubation with $5\times10^5$ 'L' cells in an ideally same environment as that of *N. sativa* plant extract.

Immunomodulatory evaluation indicates enhanced proliferation of the connective tissue 'L' cells in presence of *N. sativa* extract than in its absence, thereby indicating positive immunomodulatory effect of the extract. Similar results were also obtained with patient white blood cells.

Data indicates presence of an interferon inhibitor factor (IIF) in cancer patient serum due to which there is no proliferation of the 'L' cells when they were incubated with patient serum alone. IIF and lymphokine inhibitor factor (LIF) in patient serum get suppressed post treatment with *N. sativa* plant extract, thereby exhibiting enhanced proliferation of 'L' cells. The IIF cannot be identified with antibodies against interferon.

IIF is a factor which does not allow the production of autologous (self) interferon in the human body. When the inducer initiates the production of interferon, the human body produces another protein which neutralizes the possibility for production of interferon. LIF includes all factors that suppress cytokine activity, including interferons.

The increased stimulation of connective cells by the reduction of IIF and LIF allows the human body to produce its own interferon, which then interferes with controlling connective tissue cell production. For this reason, *N. sativa* has potential use in connective tissue diseases such as rheumatoid arthritis, lupus and autoimmune diseases.

Experiment 3

Cytopathic Effects of Vesicular Stomatitis Virus

Cell Line: The human amnion or "WISH" cells were obtained from the American Type Cell Culture facility (ATCC) and grown in Basal Eagle Medium (BEM) (GIBCO) with 15% fetal bovine serum.

Virus: Vesicular stomatitis virus (VSV) was obtained from the ATCC. The VSV stock solution was diluted 1000× with BEM containing 2% fetal bovine serum (FBS).

Assay: The assay was conducted as described above in Procedure 4. For determining the amount of protection conferred to the "WISH" cells by *N. sativa* plant extract, complete viral cytopathic effect (CPE) was calculated by inoculating 8–10 ml per flask of the 1:1000 VSV into each WISH cell flask (containing $3.5 \times 10^5$ cells/ml) such that it covered the entire cell layer. The flasks were incubated for 1 hour at 37° C. in a 5% $CO_2$ incubator. Fifteen ml of the BMEM with 2% FBS were added to each flask and incubated at 37° C. in a 5% $CO_2$ incubator for 1–3 days or until cell layer showed complete viral cytopathic effect (CPE). *N. sativa* plant extract was serially diluted in a 96-well polystyrene plate. To 40 µl of the extract was added 100 µl of the $3.5 \times 10^5$ cells/ml "WISH" cell suspension and the plates were incubated for approximately 18–24 hours at 37° C. at 5% $CO_2$. In the control wells, no extract was added. Next day (after 18–24 hours) the plates were observed under Nikon TMS microscope for confluency. Fifty µl VSV were added (in a concentration to yield 100% CPE), and Incubated 24–48 hours at 37° C. with 5% $CO_2$.

The next day, the plates were observed under a Nikon TMS microscope for 100% CPE in the viral control wells. Once satisfied, the plates were dumped and blotted. One hundred µl of 15% neutral red dye were added to all wells. The wells were incubated at 37° C. in 5% $CO_2$ incubator for 45 minutes. The plates were dumped, blotted and rinsed with 200 µl PBS at pH 6.85. The plates were again dumped and blotted. The cells were eluted by adding 100 µl of the eluting solution to each well. The plates were read on Bio-Rad Model 3550 microplate reader.

The concentration of vesicular stomatitis virus (VSV) producing 100% cytopathic effect (CPE) of human amniotic "WISH" cells was first determined, which was $1 \times 10^5$ plaque forming units. Optimum protection to WISH cells conferred by *N. sativa* extract was then calculated by serially diluting *N. sativa* extract and adding in between WISH cells and VSV.

Figure 2:
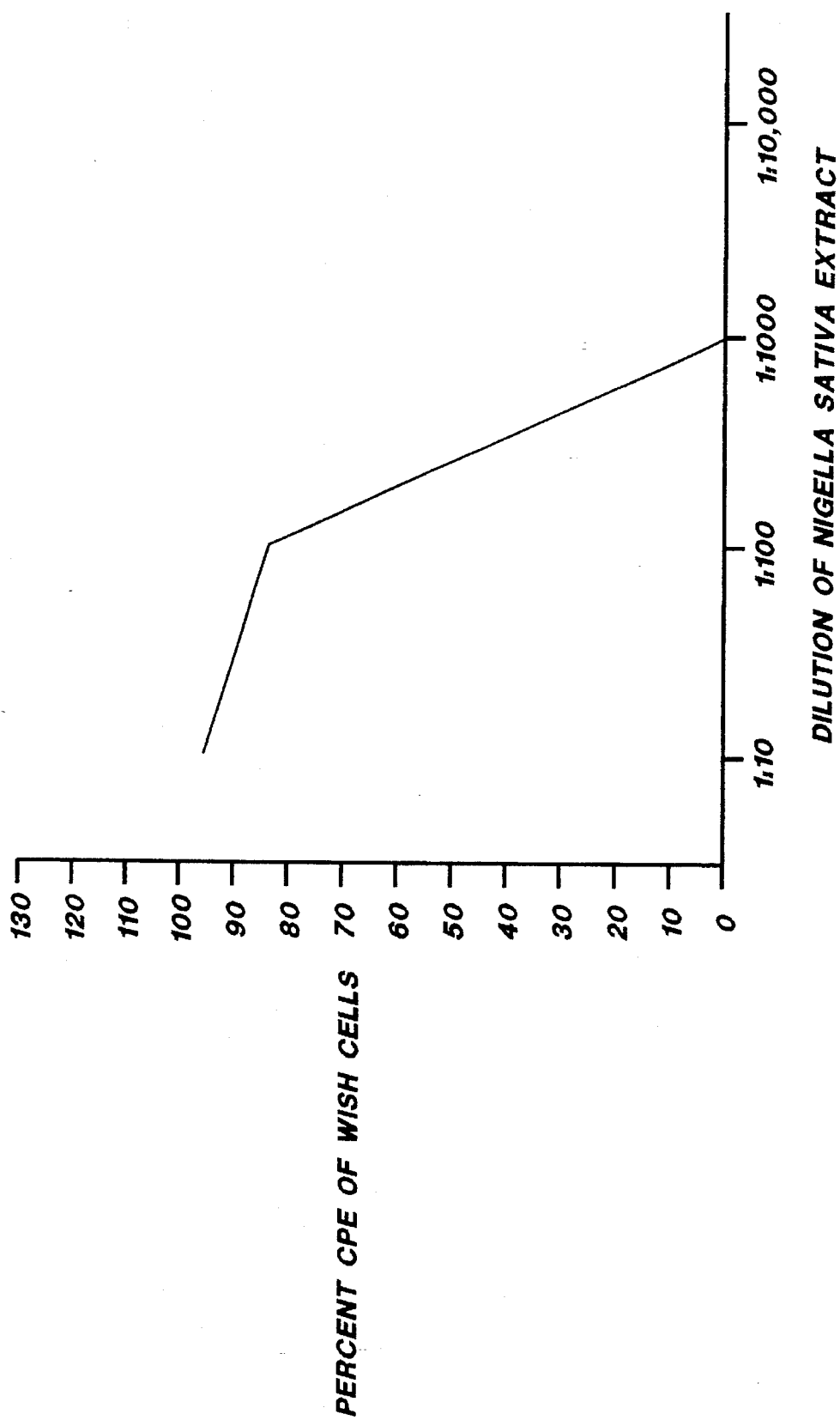
FIG. 2 is a graph illustrating the percent protection of $3.5 \times 10^4$ WISH cells from the cytopathic effects (CPE) of vesicular stomatitis virus (VSV) by serial dilutions of *N. sativa* extract as described in Experiment 3.

Results: The results depicted in FIG. 2 indicate protection of "WISH" cells in the order of 25 and 65% upon incubation with 1:10 and 1:100 diluted *N. sativa* plant extract. There was no noticeable cytopathic effect when *N. sativa* was added at a dilution of 1:1000. Approximate active compound concentrations were calculated according to materials and methods. Serum interferon levels were measured after plant extract administration according a modified procedure of Finter (1969).

Protection of Human Amniotic "WISH" cells from cytopathic effects of vesicular stomatitis virus (VSV) was observed upon administration of 1:1000 diluted *N. sativa* plant extract. This had an active compound concentration of 88 ng. At a lower dilution, there was some effect. Theoretically, a patient weighing 70 kg has about $7 \times 10^{13}$ cells in its body and *N. sativa* will be useful in the dosage of 20–40 g to protect against viral attack in virus endemic areas. Upon administration of the extract, the serum interferon level is found to increase and hence *N. sativa* has interferon-like antiviral activity. The extract possibly blocks all receptor sites on "WISH" cells which are essential for attachment of the virus to cell membrane.

Experiment 4

Pharmacosensitivity Assay

The tumor specimens can be of 2 types: solid tumor and liquid tumor.

Solid tumor: 2 grams of tumor specimen were excised, cut into pea size portions and gently homogenized in a Potter-Elvehjam homogenizer with 10% FBS, centrifuged at 1600 rpm for 20 minutes in a Mistral 3000i refrigerated centrifuge at 4° C. Cells were finally suspended in media RPMI 1640 with 10% FBS into a fine suspension.

Liquid tumor: The specimen was collected from the ascitic fluid of cancer patients. The ascitic fluid was gently layered on a histopaque using a 1:1 ratio of the histopaque to specimen, and centrifuged at 1600 rpm for 20 minutes in a Mistral 3000i refrigerated centrifuge at 4° C. Cells were finally suspended in RPMI with 10% FBS.

Assay: The assay was performed according to the modified processes of Von Hoff, et al. (1981) and Salmon, et al. (1978), which are incorporated herein by reference, as described above in Procedure 5. Tumoricidal activity of *N. sativa* was checked on a double agar layer. The lower layer of warm 2.5% Bacto-agar working solution was poured into 35 mm grid petri dishes. The plates were then allowed to sit undisturbed on a flat surface until the agar solidified. To 2.1 ml of the upper layer media containing 150 ml FBS, 150 ml 2× G.G. fortified solution and 150 ml 1× G.G. fortified solution, 0.3 ml of the tumor cells and 0.6 ml of the 1.5% agar were added.

The upper layer was carefully layered on top of the lower layer in the 35 mm grid petri dish. Tumor specimens grown without the extract and with 'Abrin' were used as controls. Tumor cell growth in the presence of the plant extract was monitored 7, 14 and 21 days post incubation at 37° C. and 5% $CO_2$, at which time the cells were counted under a Reichert-Jung biostar inverted microscope. Cells from tumor specimens [$8.2 \times 10^4$] were grown with media/Abrin plant extract on a double agar layer and incubated for 7, 14 and 21 days at 37° C. in a humid 5% $CO_2$ incubator. The results are shown on Table 5 as follows:

TABLE 5

| INCUBATION MIXTURE | INCUBATION TIME | | | | | |
|---|---|---|---|---|---|---|
| | 7 days | % Inh | 14 days | % Inh | 21 days | % Inh |
| TUMOR CELL & MEDIA | $8.2 \times 10^4$ | 0 | $10.0 \times 10^4$ | 0 | $10.5 \times 10^4$ | 0 |
| TUMOR CELL & ABRIN | $8.1 \times 10^4$ | 1.2 | $9.8 \times 10^4$ | 2.0 | $10.3 \times 10^4$ | 1.9 |
| TUMOR CELL & EXTRACT | $5.3 \times 10^4$ | 35.0 | $5.4 \times 10^4$ | 46.0 | $5.5 \times 10^4$ | 48.0 |

The SD of the data was <10%. Percentage of inhibition was calculated as described in Materials & Methods.

The results are analyzed on the basis of pharmacosensitivity assay in which tumor cell growth was monitored. Seven, 14 and 21 days post incubation with plant extract indicated tumoricidal activity. Hence, *N. sativa* extract possessed a multifaceted toxic-free cure for cancer.

Results: Tumor specimens (2 grams) either from solid tumor masses or malignant ascites were mechanically homogenized into a suspension containing $8.2 \times 10^4$ cells. Incubation of tumor cells at 37° C. in a humid 5% $CO_2$ incubator for 7, 14 and 21 days with *N. sativa* plant extract indicated a percent inhibition of 35, 46 and 48, respectively. Incubation with Abrin in an ideally similar condition did not exhibit any noticeable inhibition.

*N. sativa* promotes anti-tumor activity. Data from pharmacosensitivity screening indicates anti-tumor activity of *N. sativa* plant extract, as cell growth in culture was inhibited anywhere between 25–90%. In vitro tumor study report, using rapid screen for early pharmacosensitivity screening, in which cells were incubated with *N. sativa* plant extract for 2 hours, gave similar results. Hence, the extract indicates anti-tumor function mainly against melanoma and colon cancer types. *N. sativa* plant extract destroys tumor cells and leaves normal cells alone, possibly because of its ability to bind to cell surface asialofeutin (lectin) in diseased cells, which causes aggregation and clumping of tumor cells. It also blocks enzymes and inappropriate gene products involved in nucleic acid synthesis and metabolism.

It is understood that the invention is not confined to the particular construction and arrangement herein described, but embraces such modified forms thereof as come within the scope of the claims following the bibliographic citations.

BIBLIOGRAPHY

Agarwal, R., Kharya, M. D., and Shrivastava, R., 1979, "Antimicrobial anthelmintic activities of the essential oil of *Nigella sativa* Linn," *Indian J. Exp. Biol.* 17, 1264.

Akhtar, M. S.; Riffat, S., 1991, "Field Trial of Saussurea Lappa Roots Against Nematodes and *Nigella Sativa* Seeds Against Cestodes in Children," *JPMA J Pak Med Assoc* 41(8)185–7.

al-Awadi, F. M., Khattar, M. A. and Gumaa, K. A., 1985, "On the Mechanism of the Hypoglycemic Effect of a Plant Extract," *Diabetologia* 28, 432–434.

al-Awadi, F.; Fatania, H.; Shamte, U., 1991, "The Effect of a Plant's Mixture Extract on Liver Gluconeogenesis in Streptozotocin Induced Diabetic Rats," *Diabetes Res (Scotland)* 18(4):163–8.

Aruna, K.; Sivaramakrishnan, V. M., 1990, "Plant Products as Protective Agents Against Cancer," *Indian J Exp Biol* 28(11):1008–11.

Aruna, K.; Sivaramakrishnan, V. M., 1992, "Anticarcinogenic Effects of Some Indian Plant Products," *Food Chem Toxicol (England)* 30(11)953–6.

Bitterman, W. A.; Farhadian, H.; Abu Samra, C.; Lerner, D.; Amoun, H.; Krapf, D;. Makov, U. E., 1991, "Environmental and Nutritional Factors Significantly Associated with Cancer of the Urinary Tract among Different Ethnic Groups," *Urol Clin North Am* 18(3)501–8.

Chopra, R. N., Chopra, I. C., Handa, K. L., and Kapur, L. D., 1982, *Indigenous Drugs of India,* Academic Publishers; Calcutta, India.

Datta, A. K., Biswas, A. K. and Ghosh, P. D., 1983, "Chromosomal variations in callus tissues of two species of *Nigella sativa,* L.," *The nucleus* 26(3) 173–177.

Elkadi, A ; Kandil, O., 1987, "The Black Seed *Nigella sativa* and Immunity Its Effects on Human Cell Subsets," *Fed Proc* 45(4)1222.

Finter, N. B., 1969, "Dye Uptake Methods for Assessing Viral Cytopathogenicity and Their Application to Interferon Assays, " *J. Gen. Virol.* 5, 419–427.

Karen, D. F., 1989, "Flow Cytometry in Clinical Diagnosis," *American Society of Clinical Pathology* (press).

Kirtikar, K. R. and Basu, B. D., 1982, *Indian Medicinal Plants, Vol. I*, Bishen Singh and Mahendra Pal Singh, eds., Dehra Dun, India.

Kumar, B. H. and Thakur, S. S., 1989, "Effect of Certain Non-edible Seed Oils on Growth Regulation in Disdercus Similis (F), *J. Anim. Morphol. Physiol.* 36(2) pp. 209–218.

Medenica, R., Alonso, K., Huschart, T. and Tyler, K., 1990, "Tumor Tissue Culture for Determining Efficient Drug for Intra-Arterial, Intra-Hepatic Chemotherapy and Interferon of Colon Carcinoma Liver Metastasis," *Abstract presented at Conference on Combining BRM with Cytotoxic in the Treatment of Cancer.*

Merkel, D. E., Dressier, L. G. and McGuire, W. L., 1987, "Flow Cytometry Cellular DNA Contents and Prognosis in Human Malignancy," *J. of Clinical Oncology,* 5, 1690–1703.

Metcalf, D., 1984, *Clonal Culture of Hematopoietic Cells,* Elsevier/North American Biomedical Press.

Metcalf, D., 1985, "The Granulocyte Macrophage Colony Stimulating Factors," *Science* 229, 16–22.

Nadkarni, K. M., 1976, *"Crocus sativus, Nigella sativa," Indian Materia Medica,* K. M. Nadkarni (ed) Bombay, India; Popular Prakashan, Vol 1, pg. 386–411.

Nair, S. C.; Salomi, M. J.; Panikkar, B.; Pannikar, K. R., 1991, "Modulatory Effects of *Crocus sativus* and *Nigella sativa* Extracts on Cisplatin-Induced Toxicity in Mice," *J Ethnopharmocol* 31(1): 75–83.

Salmon, S. E., Hamburger, A. W., Soehnlein, B., 1978, "Quantitation of Differential Sensitivity of Human Tumor Stem Cells to Anticancer Drugs, , " *N. Eng. J. Med.* 298, 1321–1327.

Salomi, N. J.; Nair, S. C.; Jayawardhanan, K. K.; Varghese, C. D.; Panikkar, K. R., 1992, "Anititumour Principles from *Nigella sativa* Seeds," *Cancer Lett* 63(1):41–6.

Salomi, M. J.; Nair, S. C.; Panikkar, K. R., 1991, "Inhibitory Effects of *Nigella sativa* and Saffron (Crocus Sativus) on Chemical Carcinogenesis in Mice," *Nutr Cancer* 16(1):67–72.

Sayed, M. D., "Traditional Medicine in Health Care," 1980, *J Ethnopharmocol* 2(1):19–22.

Shayeb, N. A. and Mabrouk, S. S., 1984, "Utilization of Some Edible and Medicinal Plants to Inhibit Aflatoxin Formation," *Nutrition Reports International* 29(2).

Siddiqui, M. B., Alam, M. M., Husain, W. and Sharma, G. K., 1988, "Ethno-medical Study of Plants used for Terminating Pregnancy," *Fitoterapia* V. LIX, no. 3, 250.

Salmon, S. E.; Hamburger, A. W.; Soehnlein, B.; et al., 1978, "Quantitation of differential sensitivity of human tumor stem cells to anticancer drugs," *N Engl J Med* 298:1321–1327.

Srivastava, K. C., 1989, "Extracts from Two Frequently Consumed Spices—Cumin (Cuminum cyminum) and Turmeric (Curcuma Longa)—Inhibit Platelet Aggregation and Alter Eicosanoid Biosynthesis in Human Blood Platelets," *Prostaglandins Leukot Essent Fatty Acids* 37(1)57–64.

Tennekoon, K. H.; Jeevathayaparan, S.; Kurukulasooriya, A. P.; Karunayake, E. H., 1991, "Possible Hepatotoxicity of *Nigella sativa* Seeds and Dregea Volubilis Leaves," *J Ethnopharmocol* 31(3):283–9.

Vihan, V. S. and Panwar, H. S., 1987, "Galactopoietic Effect of *Nigella sativa* (H-Kalonji) in Clinical Cases of Agalactia in Goats, " Indian Vet. J. 64, 347–349.

Von Hoff, D. D., Cowan, J., Harris, J. and Reisdorf, G., 1981, "Human Tumor Cloning: Feasibility and Clinical Correlations," *Cancer Chemother. Pharmacol.* 6, 265–271.

I claim:

1. A method for activating immune competent cells in humans in order to increase the immune function in humans, the immune competent cells being selected from the group consisting of CD19, HLADR, NKCD3–/CD56+ and CD38, the method comprising administering to humans an effective dose of an extract from *Nigella sativa* at a concentration which is effective to activate the immune competent cells by reducing the presence of interferon inhibitor factor or lymphokine inhibitor factor.

2. The method of claim 1 wherein the effective dose is between about 20 and about 40 grams of the extract per day.

3. The method of claim 1 wherein the effective dose is about 30 grams of the extract per day.

4. A method for increasing antibody producing B cells in humans, the B cells having minor antigen binding sites, comprising administering to humans an effective dose of an extract from *Nigella sativa*, at a concentration which is effective to free the tumor antigen binding sites on the B cells thereby increasing the antibody producing B cells.

5. The method of claim 4 wherein the effective dose is between about 20 and about 40 grams of extract per day.

6. The method of claim 4 wherein the effective dose is about 30 grams of extract per day.

\* \* \* \* \*